(12) United States Patent
Knapp

(10) Patent No.: US 8,764,847 B2
(45) Date of Patent: Jul. 1, 2014

(54) STENT

(75) Inventor: Tracey Knapp, Lawrenceville, GA (US)

(73) Assignee: C. R. Bard, Inc., Covington, GA (US)

( * ) Notice: Subject to any disclaimer, the term of this patent is extended or adjusted under 35 U.S.C. 154(b) by 414 days.

(21) Appl. No.: 13/119,412

(22) PCT Filed: Sep. 16, 2009

(86) PCT No.: PCT/US2009/057156
§ 371 (c)(1),
(2), (4) Date: May 6, 2011

(87) PCT Pub. No.: WO2010/033592
PCT Pub. Date: Mar. 25, 2010

(65) Prior Publication Data
US 2011/0230950 A1     Sep. 22, 2011

Related U.S. Application Data

(60) Provisional application No. 61/097,514, filed on Sep. 16, 2008.

(51) Int. Cl.
*A61F 2/04* (2013.01)
(52) U.S. Cl.
USPC ........................................... 623/23.66; 604/8
(58) Field of Classification Search
CPC ..... A61F 2/04; A61F 2/042; A61F 2002/048; A61F 2002/047
USPC ............... 623/23.64–23.76, 1.11, 1.15; 604/8
See application file for complete search history.

(56) References Cited

U.S. PATENT DOCUMENTS

| | | | | |
|---|---|---|---|---|
| 4,334,327 A | * | 6/1982 | Lyman et al. | 623/23.66 |
| 4,531,933 A | | 7/1985 | Norton et al. | |
| 4,740,207 A | * | 4/1988 | Kreamer | 623/1.15 |
| 4,813,925 A | * | 3/1989 | Anderson et al. | 604/8 |
| 4,973,301 A | * | 11/1990 | Nissenkorn | 604/8 |
| 5,486,191 A | * | 1/1996 | Pasricha et al. | 606/191 |

(Continued)

FOREIGN PATENT DOCUMENTS

FR        2 557 460 A1     7/1985

OTHER PUBLICATIONS

International Search Report and Written Opinion dated Nov. 6, 2009 for PCT/US2009/057156.

(Continued)

*Primary Examiner* — Alvin Stewart
(74) *Attorney, Agent, or Firm* — Knobbe Martens Olson & Bear, LLP

(57) ABSTRACT

A stent is deployed within a body passageway. The stent is configured to curl a varying degree upon itself as the stent is inserted into the passageway depending on the size of the passageway. In this way a single size stent may be employed in different size passageways. The stent may have a generally rectangular shape or other shape. The stent may be made of one or more materials. For example, a spine of the stent may be made of a material different than a material used for the outer edges of the stent. The edges of the stent curl towards the spine during insertion into the passageway without any further manipulation of the stent or by application of any additional mechanical means. The stent may have a varying thickness and/or width along the longitudinal axis of the stent.

27 Claims, 21 Drawing Sheets

(56) References Cited

U.S. PATENT DOCUMENTS

| | | | |
|---|---|---|---|
| 5,507,824 A * | 4/1996 | Lennox | 623/22.25 |
| 5,618,299 A | 4/1997 | Khosravi et al. | |
| 5,647,843 A * | 7/1997 | Mesrobian et al. | 604/8 |
| 5,776,160 A * | 7/1998 | Pasricha et al. | 606/191 |
| 5,782,928 A * | 7/1998 | Ries et al. | 623/22.21 |
| 5,833,707 A | 11/1998 | Mcintyre et al. | |
| 5,972,032 A * | 10/1999 | Lopez et al. | 623/22.32 |
| 5,984,963 A | 11/1999 | Ryan et al. | |
| 5,989,207 A * | 11/1999 | Hughes | 604/8 |
| 6,017,362 A | 1/2000 | Lau | |
| 6,162,237 A | 12/2000 | Chan | |
| 6,214,037 B1 * | 4/2001 | Mitchell et al. | 623/1.11 |
| 6,395,021 B1 | 5/2002 | Hart et al. | |
| 6,514,284 B1 * | 2/2003 | Cheng | 623/1.15 |
| 6,620,202 B2 * | 9/2003 | Bottcher et al. | 623/23.7 |
| 6,656,146 B1 * | 12/2003 | Clayman et al. | 604/8 |
| 6,709,465 B2 | 3/2004 | Mitchell et al. | |
| 6,719,804 B2 * | 4/2004 | St. Pierre | 623/23.7 |
| 6,776,194 B2 * | 8/2004 | Houston et al. | 138/39 |
| 6,929,664 B2 * | 8/2005 | Kolb | 623/23.66 |
| 6,945,950 B2 | 9/2005 | Clayman et al. | |
| 7,022,142 B2 * | 4/2006 | Johnson | 623/22.24 |
| 7,044,981 B2 * | 5/2006 | Liu et al. | 623/23.66 |
| 7,074,241 B2 * | 7/2006 | McKinnon | 623/22.24 |
| 7,217,250 B2 * | 5/2007 | Kolb | 604/8 |
| 7,316,663 B2 * | 1/2008 | Whitmore, III | 604/8 |
| 7,338,530 B2 * | 3/2008 | Carter et al. | 623/23.66 |
| 7,572,296 B2 * | 8/2009 | Scott et al. | 623/22.28 |
| 7,625,408 B2 * | 12/2009 | Gupta et al. | 623/21.11 |
| 7,628,819 B2 * | 12/2009 | Gupta et al. | 623/21.11 |
| 7,674,283 B2 * | 3/2010 | Mitchell et al. | 623/1.3 |
| 7,682,398 B2 * | 3/2010 | Croxton et al. | 623/22.24 |
| 7,972,292 B2 * | 7/2011 | Behl et al. | 604/8 |
| 8,021,434 B2 * | 9/2011 | Segura et al. | 623/23.7 |
| 8,057,534 B2 * | 11/2011 | Boismier et al. | 623/1.38 |
| 8,080,019 B2 * | 12/2011 | Behl et al. | 606/127 |
| 8,088,170 B2 * | 1/2012 | Whitmore, III | 623/23.7 |
| 8,118,876 B2 * | 2/2012 | Gupta et al. | 623/21.11 |
| 8,206,454 B2 * | 6/2012 | Hormansdorfer | 623/22.31 |
| 8,226,704 B2 * | 7/2012 | Caro et al. | 623/1.17 |
| 8,231,686 B2 * | 7/2012 | Mangiardi | 623/23.7 |
| 8,241,548 B2 * | 8/2012 | Gellman | 264/279.1 |
| 8,246,691 B2 * | 8/2012 | Mangiardi | 623/23.69 |
| 8,398,705 B2 * | 3/2013 | Mangiardi | 623/1.15 |
| 2003/0040754 A1 * | 2/2003 | Mitchell et al. | 606/106 |
| 2003/0171708 A1 * | 9/2003 | Segura et al. | 604/8 |
| 2003/0195456 A1 | 10/2003 | Robertson | |
| 2003/0199986 A1 * | 10/2003 | McWeeney et al. | 623/23.7 |
| 2003/0199993 A1 | 10/2003 | Gellman et al. | |
| 2004/0059279 A1 | 3/2004 | McWeeney | |
| 2004/0073283 A1 * | 4/2004 | Ewers | 623/1.11 |
| 2004/0249470 A1 | 12/2004 | Whitmore, III | |
| 2005/0125072 A1 * | 6/2005 | Kolb | 623/23.7 |
| 2005/0240141 A1 | 10/2005 | Aliski | |
| 2005/0240277 A1 | 10/2005 | Aliski | |
| 2006/0100689 A1 * | 5/2006 | Pryor | 623/1.12 |
| 2006/0259151 A1 | 11/2006 | Ward | |
| 2006/0265051 A1 | 11/2006 | Caro et al. | |
| 2008/0183299 A1 | 7/2008 | Monga | |
| 2008/0288047 A1 * | 11/2008 | Friebe et al. | 623/1.15 |
| 2009/0088865 A1 * | 4/2009 | Brehm | 623/22.21 |
| 2010/0198359 A1 * | 8/2010 | Ward | 623/23.66 |
| 2010/0331992 A1 * | 12/2010 | Podolsky | 623/22.15 |
| 2011/0009975 A1 * | 1/2011 | Allen et al. | 623/22.24 |
| 2011/0230950 A1 * | 9/2011 | Knapp | 623/1.11 |
| 2012/0083899 A1 * | 4/2012 | Whitmore, III | 623/23.66 |
| 2012/0116527 A1 * | 5/2012 | Birkbeck et al. | 623/22.38 |
| 2012/0303134 A1 * | 11/2012 | Amos, Jr. | 623/23.66 |
| 2013/0253662 A1 * | 9/2013 | Lamson et al. | 623/23.66 |

OTHER PUBLICATIONS

Extended Search Report for European Patent Application No. 09815117.8 dated Dec. 13, 2013.

* cited by examiner

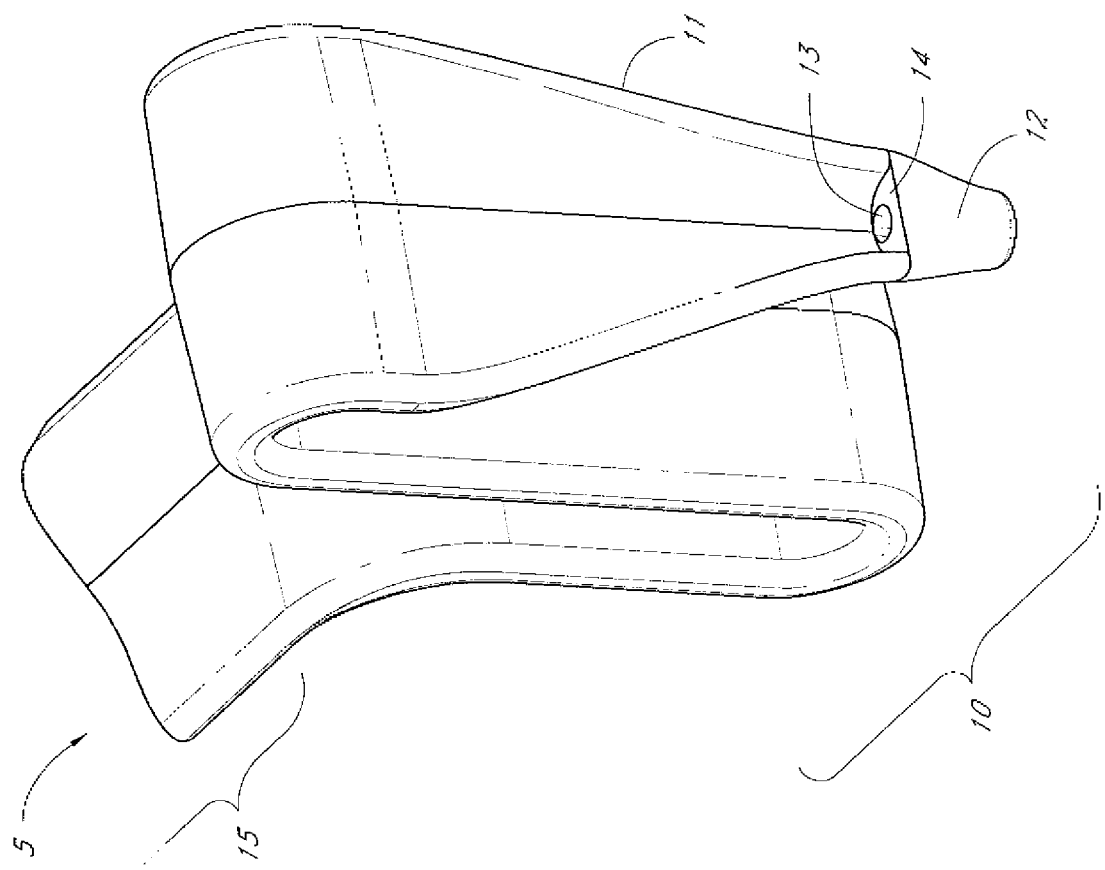

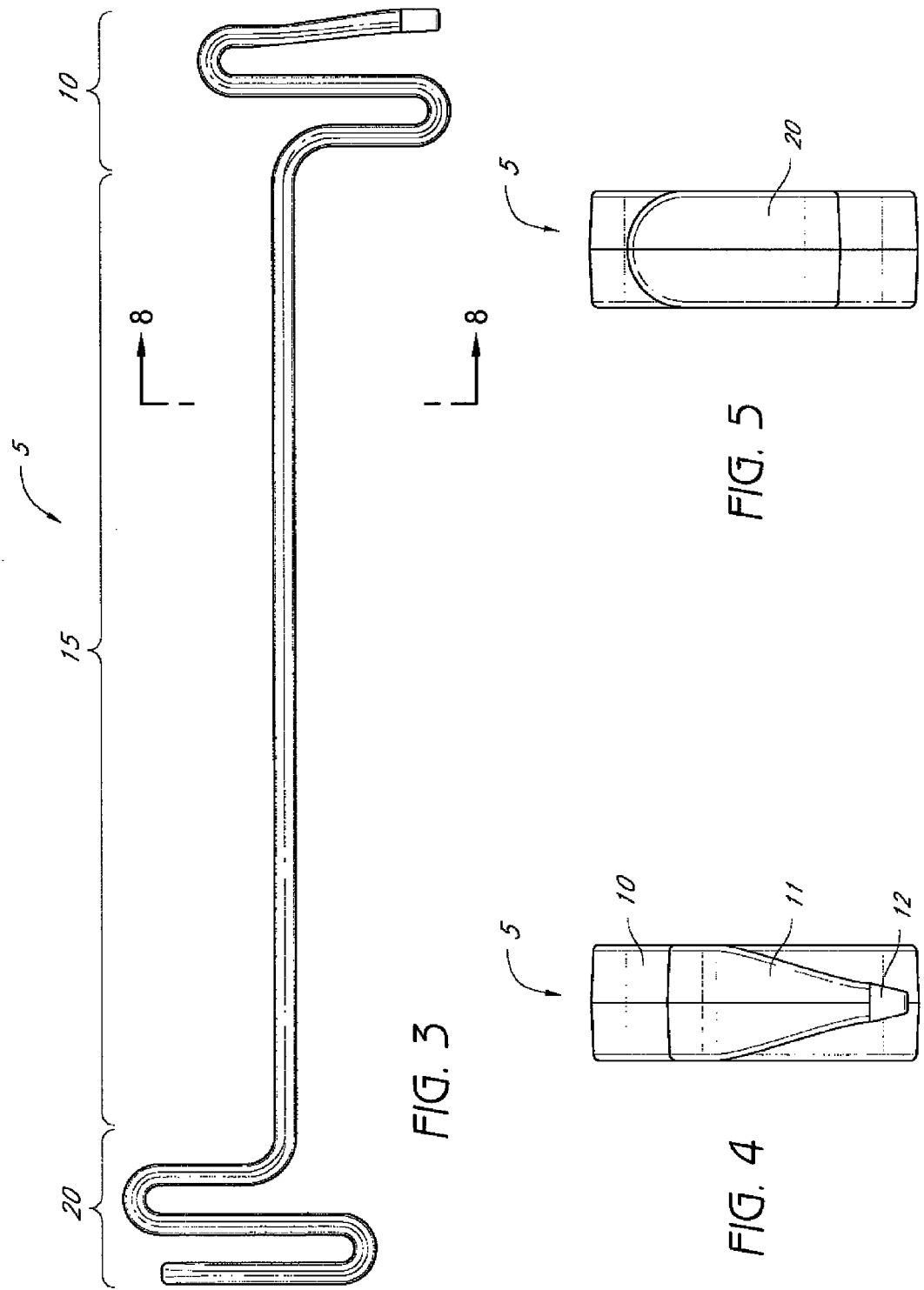

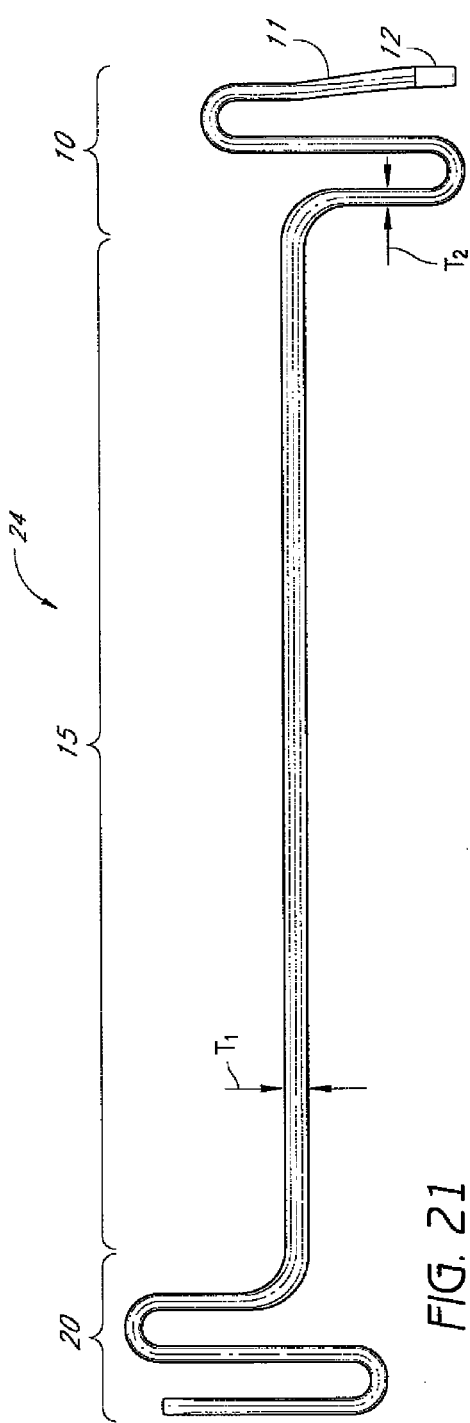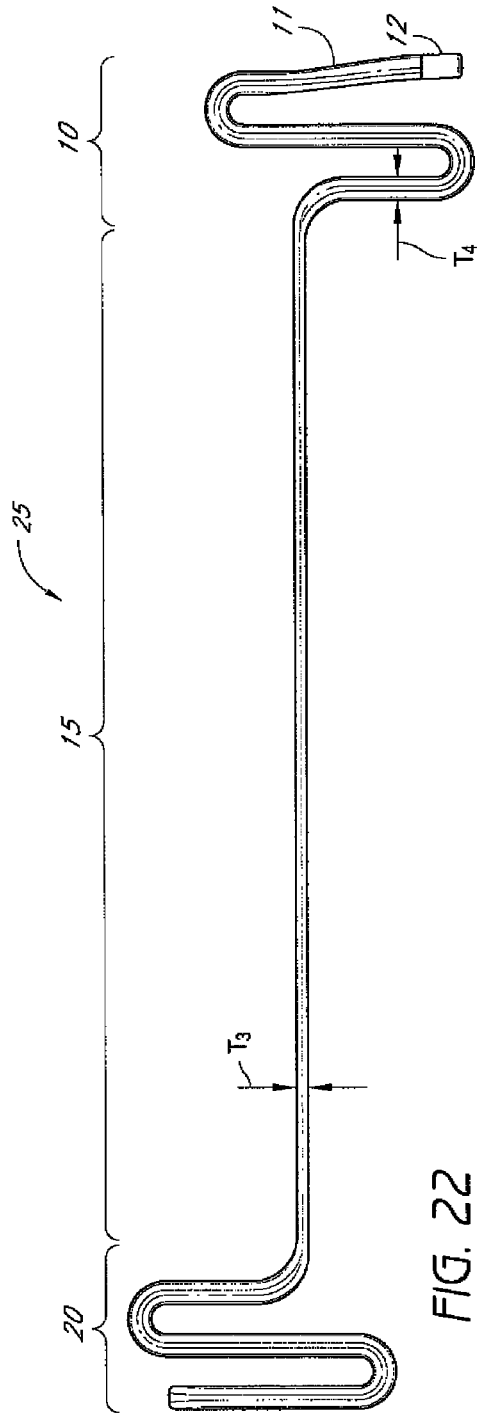

STENT

RELATED APPLICATION

This application is the National Stage of International Application No. PCT/US2009/057156, filed on Sep. 16, 2009, entitled "STENT," which claims the benefit of U.S. Provisional Patent Application No. 61/097,514, titled "STENT", filed Sep. 16, 2008. The disclosure of each of the above-reference applications is considered part of the disclosure of this application and is incorporated by reference herein.

BACKGROUND

1. Field of the Invention

The present invention relates generally to a medical device, and more particularly to a stent.

2. Description of the Related Art

Medical devices commonly known as stents have been used to reinforce and strengthen damaged body passages such as the ureter, the urethra, bile ducts, blood vessels, the trachea, coronary arteries, the gastro intestinal tract, and the esophagus. For example, blood vessels can collapse, dilate, become partially occluded or otherwise damaged by disease or other causes. An aneurysm or stricture in the blood vessel often requires a stent to strengthen the vascular wall in the area of the damage. Stents can also be used to help prevent kinking or occlusion of blood vessels such as veins or arteries and to prevent their collapse after dilatation or other treatment.

Stents can be broadly divided into two main categories: balloon expandable stents and self-expanding stents. For balloon expandable stents, the material of the stent is deformed through the inflation of a balloon, so that after the balloon is deflated the stent remains in the deployed state. Such stents are manufactured in a collapsed or delivery state, ready for delivery, and may be expanded to the deployed state when inside the body passageways.

Self-expanding stents are also delivered in a delivery state and when released from a constraining delivery system the stent expands to its deployed state of a predetermined size. This effect is often achieved by using the elasticity of the material and/or a shape-memory effect.

Traditional stents may have a fixed diameter. Because of this, a hospital may need to maintain an inventory of multiple stents each with a different diameter because each patient may have different sized body passageways. Also, traditional stents are hard to deploy and remove from body passageways as they need to be preset into a delivery state in order to fit within a body passageway. After traditional stents are deployed, they are reset into the delivery state so that they can be removed from the body passageway.

Therefore, a need continues to exist for a stent which may be used in a variety of body passageways, and is easy to deploy, remove and manufacture.

SUMMARY

In one embodiment, a stent for insertion into a lumen is provided. The stent comprises a proximal portion and a distal portion. The stem further comprises a body portion disposed between the proximal and distal portions and having an upper surface and a lower surface, the lower surface substantially conforming to an inner surface of the lumen as the body portion is inserted into the lumen.

In another embodiment, a self-deploying stent for placement in a lumen is provided. The stent comprises a body member comprising a pliant material and being movable between a first cross-sectional shape when in a delivery state and a second cross-sectional shape when in a deployed state, the first cross-sectional shape having an overall width greater than an inside diameter of the lumen, and the body member being movable from the first cross-sectional shape to the second cross-sectional shape while the stent is being inserted into the lumen.

In yet another embodiment, a self-deploying stent for placement in a lumen is provided. The stent comprises a body member being movable between a first cross-sectional shape and a second cross-sectional shape so that when a first portion of the body member is disposed inside the lumen and a second portion of the body member is disposed outside the lumen the first portion has the second cross-sectional shape and the second portion has the first cross-sectional shape, the first cross-sectional shape having an overall width greater than an inside diameter of the lumen.

In a further embodiment, a method of using a stent is provided. The method comprises aligning a stent having an overall width that is greater than a width of a lumen with an opening into the lumen. The method further comprises pushing a portion of the stent through the opening and into the lumen and as the stent is entering the opening, curling the inserted portion of the stent to substantially conform to an inside surface of the lumen before the entire stent is inserted into the lumen.

BRIEF DESCRIPTION OF THE DRAWINGS

The above mentioned and other features of the invention will now be described with reference to the drawings of several embodiments of the stent. The illustrated embodiments of the stent are intended to illustrate, but not to limit the invention. The drawings contain the following figures:

FIG. 2 is a close-up perspective view of the proximal portion of the stent from FIG. 1.

FIG. 3 is a side view of the stent from FIG. 1.

FIG. 4 is a front view of the stent from FIG. 1 and shows the proximal portion of the stent.

FIG. 5 is a back view of the stent from FIG. 1 and shows the distal portion of the stent.

FIG. 21 is a side view of a stent according to another preferred embodiment of the present invention and shows thicknesses, T1 and T2, of the stent varying along the longitudinal length of the stent.

FIG. 22 is a side view of another stent that has a varying thickness along the longitudinal length of the stent.

DETAILED DESCRIPTION OF CERTAIN EMBODIMENTS

The following description and examples illustrate certain embodiments of a stent disclosed in the context of use with an exemplary passageway or lumen. More specifically, the embodiments relate to a stent and that may used in a variety of body passageways. The stent is configured to be easily deployed and easily removed from body passageways. Embodiments of the stent are illustrated as having a generally flat shape in the lateral direction prior to insertion and a generally curved shape after insertion. However, the invention is not limited to stents that have a generally flat shape or geometry but further include stents that have a slight curve in the lateral direction prior to insertion. The curve in the lateral direction preferably is greater than a diameter of the passageway into which the stent is inserted so that the stent will curl to form a smaller diameter than the diameter of the curved stent prior to insertion. Thus, the invention includes flat as well as curved stents.

The stent is also configured to be used with different body passageways having different diameters. The principles of the present invention, however, are not limited to the body passageways such as those shown. It will be understood by those of skill in the art in view of the present disclosure that the stent described can be used with other types of medical articles and medical articles of differing sizes, including, but not limited to guide catheters, push catheters, balloon catheters, and any other device or article that may be used in conjunction with stents. Thus, the illustrations and descriptions of the stent described herein are merely examples of possible applications of the stent.

Figure 1:
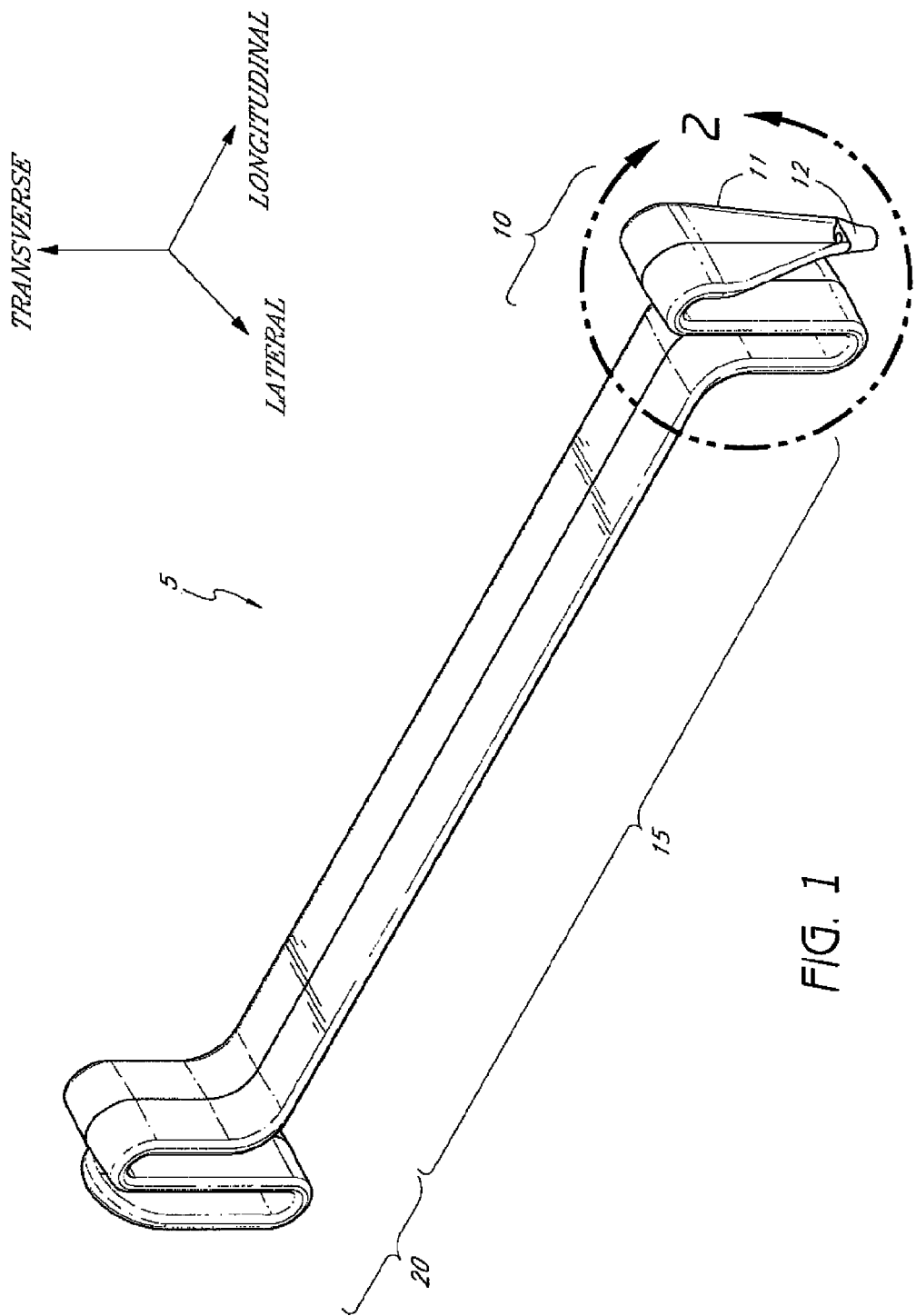
FIG. 1 is a perspective view of a stent according to a preferred embodiment of the present invention and shows a proximal portion, a main body portion, and a distal portion.

A detailed description of embodiments of a stent, and its associated method of use, now follows. With reference now to FIG. 1, an embodiment of a stent 5 includes a proximal portion 10, a main body portion 15, and a distal portion 20. The stent 5 is configured to be deployed within a body passageway. The main body portion 15 has a length greater than its width, resulting in an elongated shape. The proximal portion 10 can include a tapered frame 11 and a guide portion 12 to facilitate insertion of the stent in the passageway. However, the stent is not limited to embodiments that include a tapered frame 11.

In the illustrated embodiment, the proximal portion 10 and the distal portion 20 each include a retention curve. The retention curve is configured to prevent migration of the stent after insertion and serves to anchor the stent in the selected body cavity. During operations and medical procedures during which stents are deployed, the stent may move or migrating during the operation or procedure. A retention curve will help prevent the movement or migration of the stent once it has been deployed. The retention curve provides resistance against the openings of the body passageway and thus helps prevent the stent from moving or migrating through the body passageway.

In the embodiment shown in FIG. 1, the proximal portion 10 and the distal portion 20 are configured to naturally maintain an S-shaped retention curve when the stent is viewed from a side view such as FIG. 3. While the proximal portion 10 and the distal portion 20 may be pulled flat, they will revert back to an S-shape when the pressure resulting from the pulling is released. This reversion may be achieved by using the elasticity of the material of the stent 5 and/or a shape-memory effect. Although an S-shaped retention curve is described in the embodiment shown in FIG. 1, it will be understood by those of skill in the art that a variety of shapes may be used to create a retention curve. For example, a pig-tailed shape curved may be used. The S-shaped retention curve shown FIG. 1 is merely exemplary of one possible shape that may be used. Further, the stent 5 need not include any retention curves and according may have a generally flat shape along the entire longitudinal length of the stent.

The proximal portion 10 of the stent 5 is configured to assist in the deployment of the stent into a body passageway. The tapered frame 11 facilities the threading of the stent 5 into a body passageway. The guide portion 12 is configured to accept a guide wire which may be used to guide the stent 5 as it is inserted into a body passageway. The guide portion 12 is also configured to accept a push catheter which may be used to deploy the stent 5 into the body passageway.

The stent 5 may include at least one type of soft and/or pliable material. The material is soft enough such that it will conform to the lumen of a body passageway as the stent 5 is inserted into the body passageway. The material is also strong enough such that the stent 5 is able to provide support for the body passageway or maintain the body passageway at a certain diameter. The material of the stent may include at least one of silicone, polyurethane, a polyethylene blend, stainless steel, a metal, a metal alloy, and Nitinol materials. The material of the stent may also be elastic, stretchable, may have a shape-memory effect and may soften when subjected to heat.

To assist in the description of the components of embodiments of the stent 5, the following coordinate terms are used, consistent with the coordinate axes illustrated in FIG. 1. A "longitudinal axis" is generally parallel to a length of the stent 5. A "lateral axis" is normal to the longitudinal axis and is generally perpendicular to the length of the stent 5. When the stent 5 is deployed within a body passageway, the lateral axis will be generally perpendicular to the body passageway (i.e. from the left side of the passageway to the right side of the passageway). The stent 5 forms a generally curved shape along the lateral axis when deployed within the passageway.

A "transverse axis" extends normal to both the longitudinal and lateral axes. When the stent 5 is deployed within a passageway, the transverse axis will be generally transverse to the length and width of the passageway (i.e. from the top of the passageway to the bottom of the passageway). In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis.

FIGS. 2-8 illustrate various views of the stent 5 from FIG. 1. FIG. 2 is a close-up perspective view of the proximal portion 10 of the stent 5 from FIG. 1. The proximal portion 10 includes a tapered frame 11 and a guide portion 12. The width of the tapered frame 11 decreases as the tapered frame 11 progresses towards the guide portion 12. This geometry results in tapered frame having a pointed shape which allows the stent 5 to be more easily inserted into a body passageway. As is most clearly shown in FIG. 2, the guide portion 12 includes an aperture or hole 13 and a push surface 14. In one embodiment, a guide wire may be fed through the hole 13 in order to guide the stent 5 as it is inserted into a body passageway. A push catheter may abut against the push surface 14 so as to push or advance the stent 5 through the body passageway and along a guide wire passing through the hole 13.

FIG. 3 is a side view of the stent from FIG. 1. In the embodiment shown in FIG. 3, the stent 5 has a uniform thickness along its longitudinal length. The proximal portion 10 includes a tapered frame 11 and a guide portion 12 as described earlier with respect to FIG. 2. FIG. 4 is a front view of the stent from FIG. 1 and shows the proximal portion of the stent 5. FIG. 5 is a back view of the stent from FIG. 1 and shows the distal portion 20 of the stent.

Figure 6:
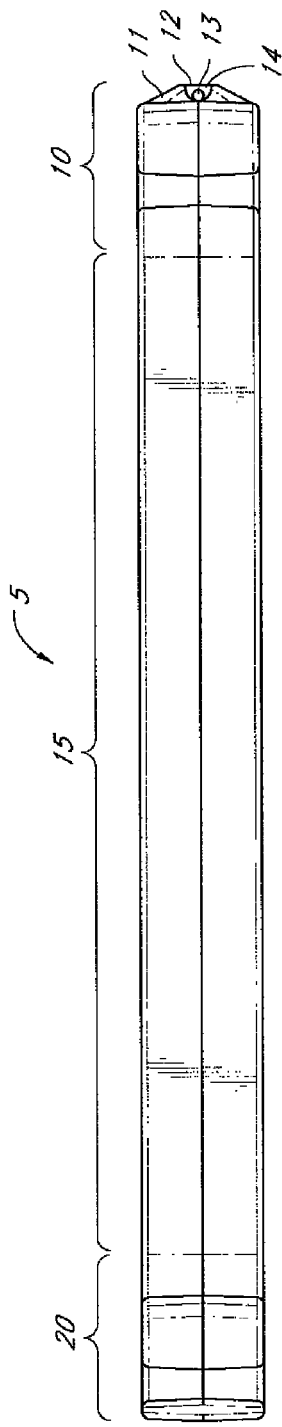
FIG. 6 is a top view of the stent from the FIG. 1.
Figure 7:
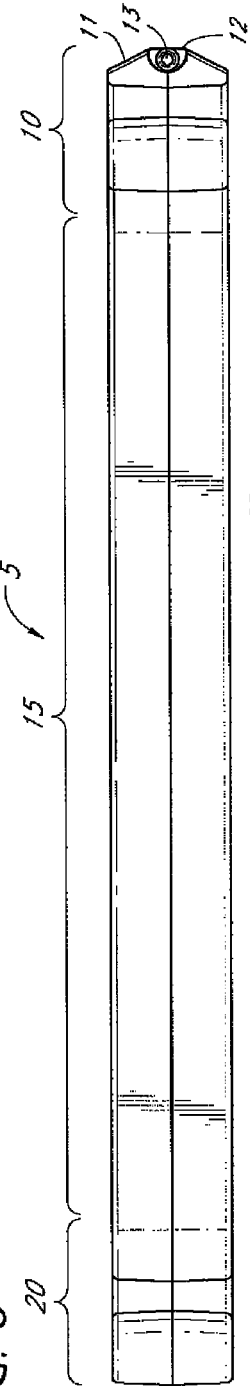
FIG. 7 is a bottom view of the stent from FIG. 1.
Figure 8:
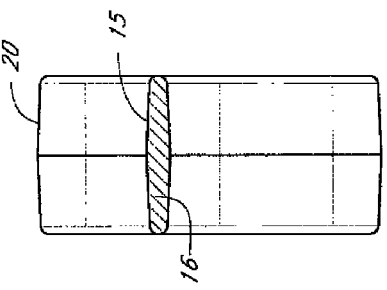
FIG. 8 is a cross sectional view through the stent from FIG. 3.

FIG. 6 is a top view of the stent 5 from the FIG. 1. FIG. 7 is a bottom view of the stent form FIG. 1. FIG. 8 is a front cross sectional view of the stent from FIG. 1, taken along the line 8-8 of FIG. 3. A cross section 16 of the main body portion 15 can be seen in this view. The proximal portion 20 is also shown as well.

Figure 9:
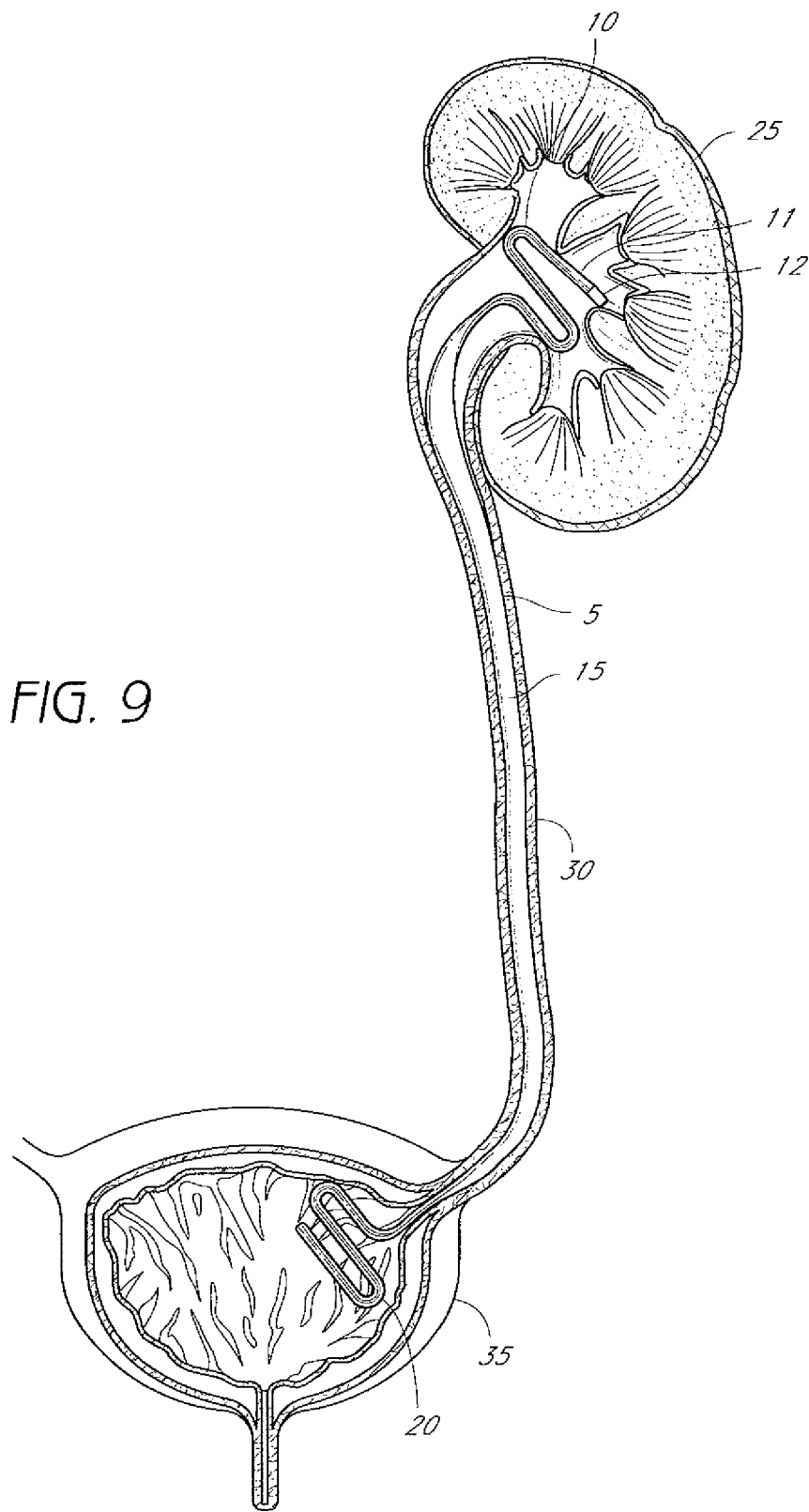
FIG. 9 is a side view of the stent from FIG. 1 deployed within a bladder, kidney and a ureter.

A method of inserting the stent 5 is described in connection with FIG. 9. FIG. 9 is a side view of the stent from FIG. 1 deployed within a bladder 35, a ureter 30 and a kidney 25. Prior to the stent 5 insertion, a guidewire is inserted into a urethra and then advanced into the bladder 35. The guidewire is then continually advanced into ureter 30 where the device is fed until reaching the kidney 25. The guide portion 12 of the stent 15 is then back-loaded onto the guidewire. The tapered frame 11 and guide portion 12 of the stent 5 are inserted into the urethra. A push catheter is next loaded onto the guidewire and advanced until contacting the push surface 14 of the stent 5. The proximal portion 10 of the stent 5 is then inserted into the bladder 35 and pushed through the ureter 30 into the kidney 25 by the push catheter.

Importantly, the cross-sectional shape of the stent 5 changes as the stent enters the ureter 30 without any further manipulation of the stent or by application of any additional mechanical means. The stent 5 preferably forms a curved shape that conforms to the inside diameter of the ureter 30 as the stent 5 enters the ureter 30. Depending on the diameter of the ureter 30 or other selected passageway, the resulting degree of curvature or diameter of the stent when in the inserted position will also vary. A common feature of the embodiments of the stent 5 is that the cross-section of the stent 5 changes as the stent 5 enters the selected passageway.

The proximal portion 10 of the stent 5 may be pushed straight as the stent 5 is being deployed within the bladder 35, the ureter 30 and the kidney 25 (i.e. the S-shaped retention curve may be straightened). After the stent has been deployed fully through the bladder 25, the ureter 30 and the kidney 35, the push catheter is removed. After the removal of the push catheter, the proximal portion 11 of the stent 5 will revert from its straightened state during deployment back towards its S-shaped retention curve. As discussed earlier in FIG. 1, the retention curves of the proximal portion 10 and the distal portion 20 of the stent 5 will help prevent the migration of the stent 5.

Figure 10:
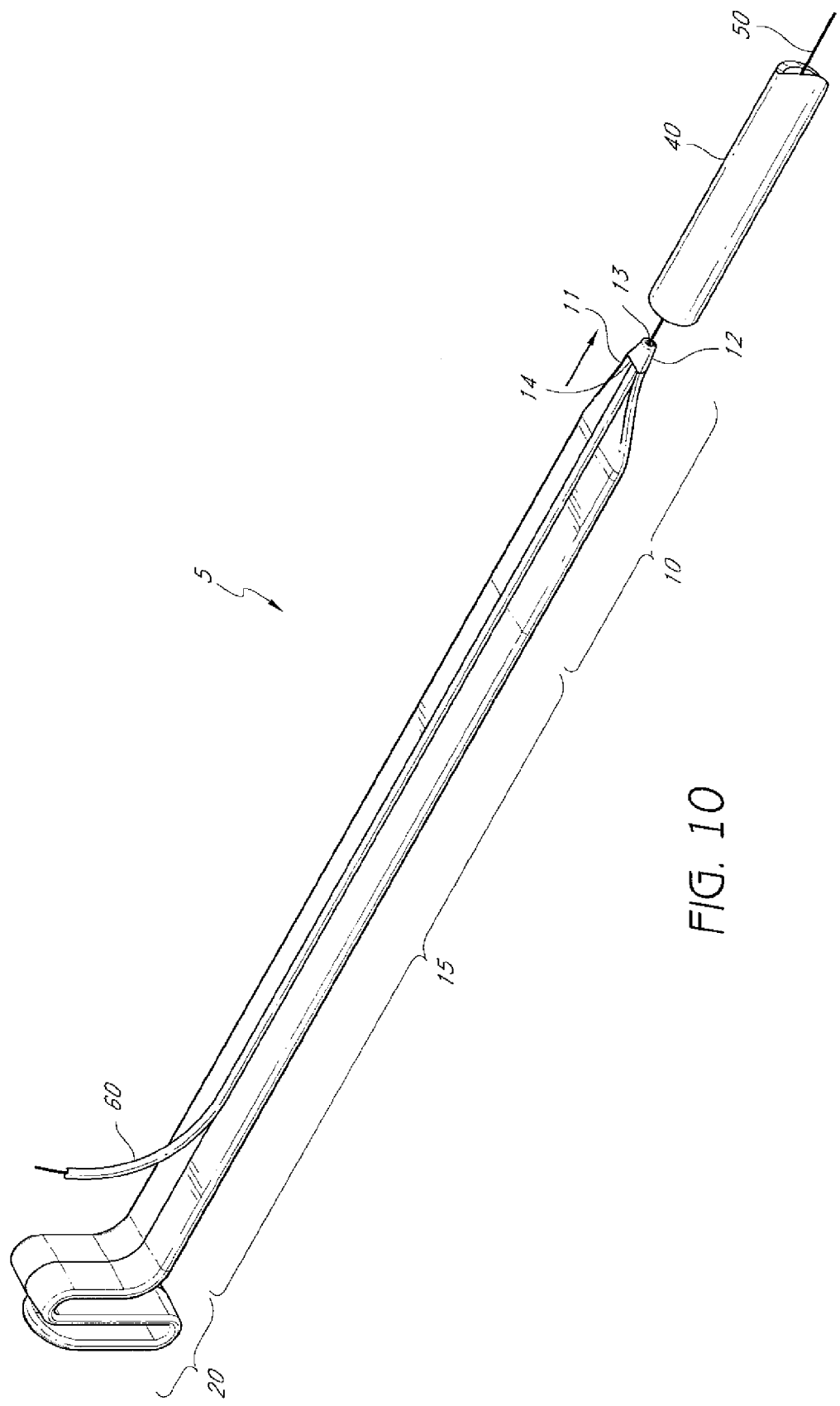
FIG. 10 is a perspective view of the stent from FIG. 1, just prior to insertion of the stent into an exemplary passageway or lumen.

FIG. 10 is a perspective view of the stent 5 just prior to insertion of the stent into a passageway 40. A guide wire 50 has been fed through the hole 13 in the guide portion 14 of the stent 5 and push catheter 60. The guide wire 50 has also been fed through passageway 40. In this embodiment, as proximal portion 10 of the stent 5 is about to be pushed or inserted into passageway 40, the retention curve of the proximal portion 10 has been pulled straight. The tapered frame 11 of the proximal portion 10 provides a pointed end which facilities feeding the proximal portion into the passageway 40 and guides the main body portion 15. The push catheter 60 may be a hollow tube comprising a material more rigid then the material of the stent 5. The push catheter 60 is configured to push the stent 5 through the passageway 40.

Figure 11:
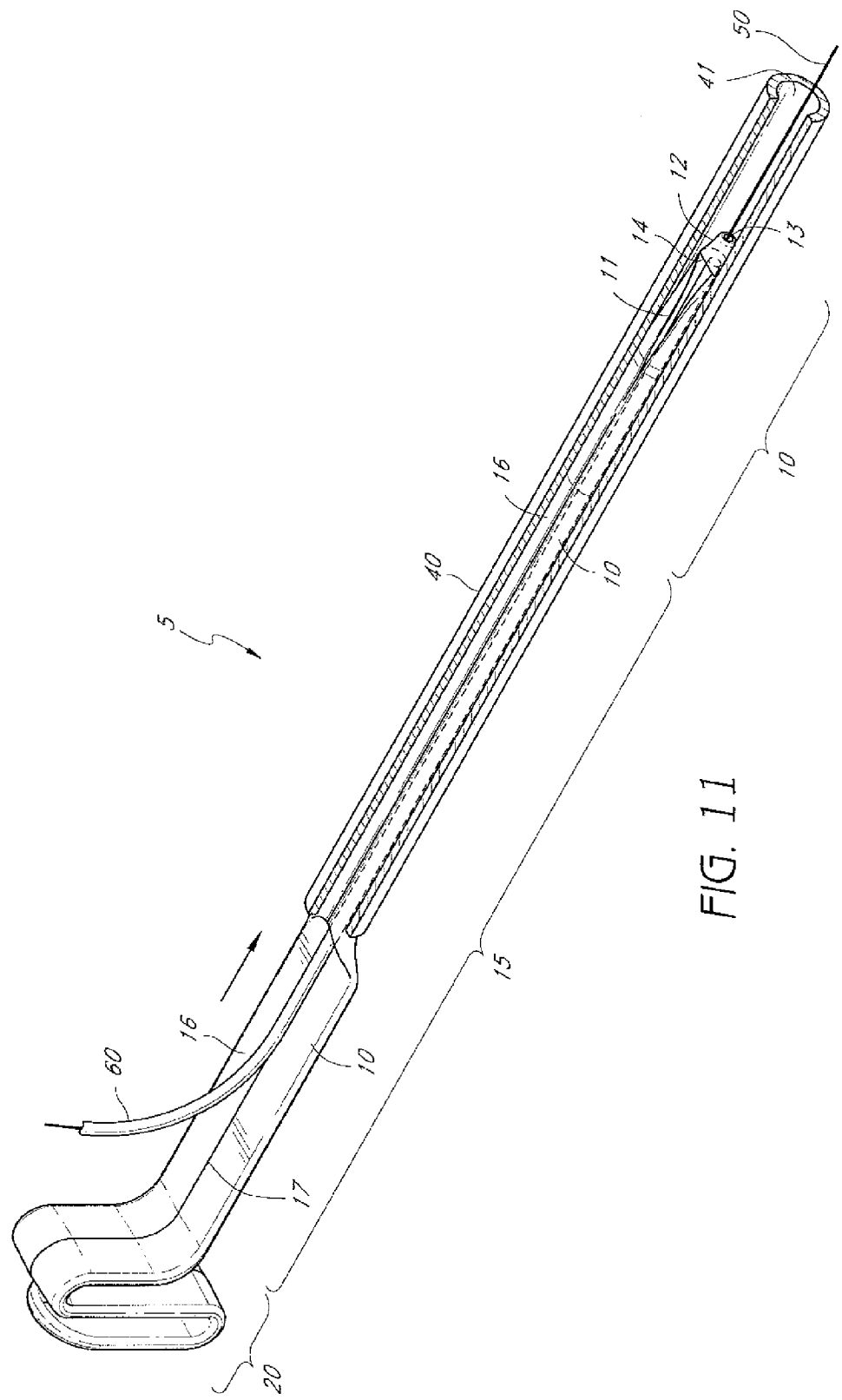
FIG. 11 is a perspective view of the stent from FIG. 10 and shows the proximal portion curling to conform to an inner surface of the passageway as the stent enters the passageway.

FIG. 11 is a perspective view of the stent 5 as the stent 5 is being deployed through a passageway 40. The proximal portion 10 as well as a portion of the main body portion 15 have been pushed into the passageway 40. Passageway 40 is illustrated in a cut-away fashion to facilitate an understanding of how the cross-section of the stent 5 changes or curves as the stent is inserted into the passageway 40. As discussed with respect to FIG. 11, the stent 5 is pushed through the passageway 40 using the push catheter 60 while being guided by the guide wire 50.

As is illustrated in FIG. 11, the stent 5 includes lateral edge portions 16 which extend along at least a portion of the longitudinal axis and on either side of a spine or center portion 17. As seen in the cutaway portion of passageway 40, the lateral edge portions 16 curl towards the center portion 17 as the stent 5 enters the passageway 40. As the stent 5 is inserted into the passageway 40, the upper or lower surface of the stent 5 contacts the inside diameter of the passageway 40 and conforms its shape to the lumen or the inner surface 41 of the passageway 40. In the illustrated embodiment, the lower surface of the main body portion 15 contacts the inner surface 41 of the passageway 40 and conforms generally to the shape or diameter of the inner surface 41. After insertion, the edge portions 16 and the center portion 17 of the stent 5 may or may not overlap. The stent 5 forms at least a groove or partial channel as it conforms to the inner surface 41 of the passageway 40. If the lateral width of the stent 5 exceeds the inside circumference of the passageway the edges of the stent may overlap assuming that the passageway does not sufficiently expand to accommodate the entire lateral width of the stent 5. For example, if the lateral width of stent 5 exceeds the inside circumference of the passageway, the stent may curl and form a spiral shape, where the edges of the stent 5 overlap each other. In another example, if the lateral width of the stent 5 is less than the inside circumference of the passageway, the lower surface of the stent may conform to the inner surface of the passageway such that the stent forms a C-shape. In another example, if the lateral width of the stent 5 is approximately equal to the inside circumference of the passageway, the lower surface of the stent may conform to the inner surface of the passageway such that the stent forms a tubular shape.

The stent 5, when in the deployed state, may partially inhibit flow through the passageway as compared to when the stent is removed from the passageway due to the stent reducing a cross-section area of the passageway. The flow rate of fluid between the kidney and bladder is relatively low so that the impact may be nominal as compared to passageways that are subject to higher flow rates. Coatings or materials may be employed on the stent 5 surface to increase flow through the passageway when the stent is deployed.

The width of the stent 5 may be selected to reduce any reduction in flow rate through the passageway. For example, it may be advantageous to select a width of the stent 5 that results in the stent forming a C-shape when deployed rather than selecting a width of the stent that results in the stent forming a spiral shape with overlapping edges when deployed. The C-shape may be more conducive to allowing flow through the passageway than the spiral shape.

As disclosed above, the stent 5 may comprise at least two different materials. For example, a first material may be softer and/or more pliable that a second material. Preferably, the materials used in the stent 5 are soft enough such that they can deform and change shape when pressure is applied to the stent 5 by the walls of the passageway 40. As the stent 5 is inserted into passageway 40, the lower surface of the stent 5 is pushed against the inner surface 41 of the passageway 40. This resulting pressure causes the soft/pliable material of the stent 5 to change shape. The edge portions 16 of the main body portion 15 conform to the inner surface 41 of the passageway 40 and curl towards the center portion 17. This curling or conforming to the inner surface 41 causes the portions of the stent which are within the passageway 40 to form a generally groove-like or tubular shape. Although not shown in the figures, the edge portions 16 of the stent 15 may overlap each other as they conform to the inner surface 41 of the body passageway 40.

A stent according to embodiments of the invention provide a variety of benefits. For example, manufacturing is simplified since the stent 5 has a generally flat shape. During the manufacture of typical circular stents, the inner and outer diameters of the stent must be maintained along with the circularity and the concentricity of the stent. The geometry of embodiments of the stent 5 includes a thickness and width. Thus, the stent 5 can be produced for less cost using moldings or an extrusion process. The stent 5 also allows easier coating of, for example, an encrustation inhibitor or medication since the upper and lower surfaces are accessible. An applied layer of medication may dissolve and deliver medication as the stent 5 is deployed within a body passageway. In typical tubular stents, only the outer diameter of the stent is available for coating.

Due to the stent 5 being able to curve a variable amount depending on the diameter of the passageway 40, a single size of stent 5 can be used for passageways 40 having different sizes. The single size stent 5 can be used for a variety of different diameter body passageways. Typical tubular stents have a defined outer diameter and are fitted based on the diameter of the body passageways of the patient. This results in a hospital or other facility maintaining and inventory of different diameter stents. However, the stent 5 disclosed herein will curl, or roll upon itself (as discussed above) to create a variable diameter stent, thus allowing one stent to be used for a variety of lumen diameters.

Another advantage of the stent 5 according to certain embodiments is that the soft/pliable material of the stent allows for easier deployment and removal of the stent from the body passageway. Typical variable sized stents are deployed in a delivery state. In the delivery state, the stent is rolled such that the edges overlap and the diameter of the rolled stent is smaller then the diameter of the lumen of the body passageway. After the rolled, variable sized stent is deployed or placed in the lumen, the structures which maintain the lumen in its rolled state are released and the variable sized stent may either self expand due to the elasticity of the material and/or a shape-memory effect, or it may be expanded using a balloon catheter into a deployed state. After the operation or medical procedure is completed, the variable sized stent must be re-rolled into the delivery state so that it may be removed from the body passageway.

The stent 5 may comprise softer and/or pliable materials. These materials allow the stent to conform to the inner surface of the body passageway as discussed earlier. Thus, the stent 5 need not be pre-rolled into a delivery state and can be inserted into a body passageway as is. In addition, because of the soft and/or pliable materials, the stent 5 does not need to be re-rolled into the delivery stated in order to remove the stent from the body passageway. Although not shown in FIG. 11, the distal portion 20 of the stent 5 may be pulled straight as the stent 5 is being removed from the body passage way 40. For example, distal portion 20 may include an opening or tab for attachment to a hook, suture, or other structure. If a hook is used, after the stent 5 is no longer needed, the hook can be inserted into the bladder and hooked to the stent via the opening. The hook can then be used to remove the stent 5. In another embodiment, a suture is attached to the opening or a projection on the distal portion 20 of the stent 5. After the stent is no longer needed, the suture can be used to remove the stent 5.

Figure 12:
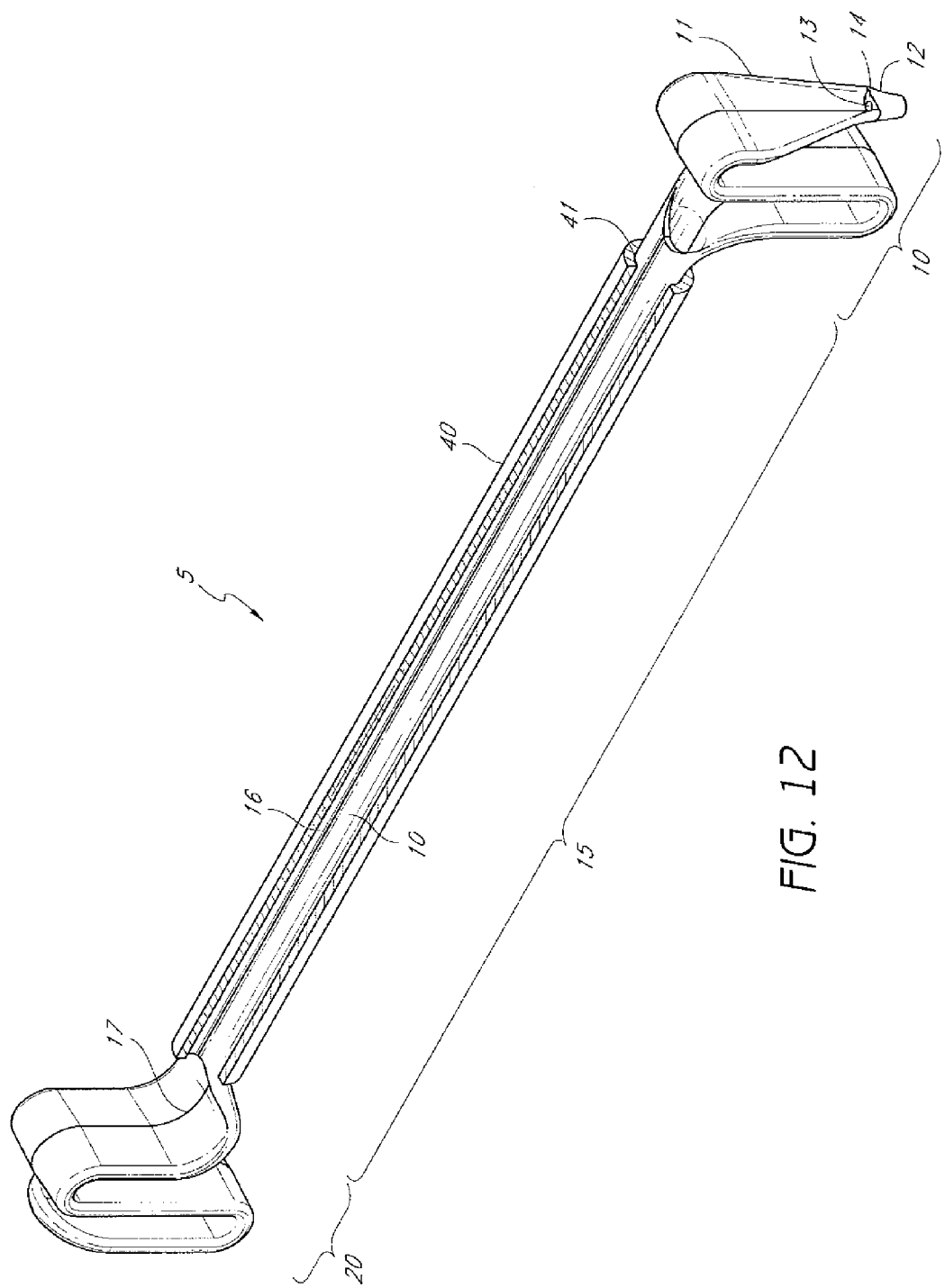
FIG. 12 is a perspective view of the stent from FIG. 11 after the stent has been deployed within the passageway with the proximal and distal portions disposed within the kidney and bladder, respectively.

FIG. 12 is a perspective view of the stent 5 deployed within a passageway 40. The edge portions 16 of the main body portion 15 are curled towards the center portion 17 such that the lower surface of the stent 5 conforms to the inner surface 41 of the passageway 40. The proximal portion 10 and the distal portion 20 have an S-shaped retention curve to prevent the stent 5 from migrating through the passageway 40 in either direction.

Figure 13:
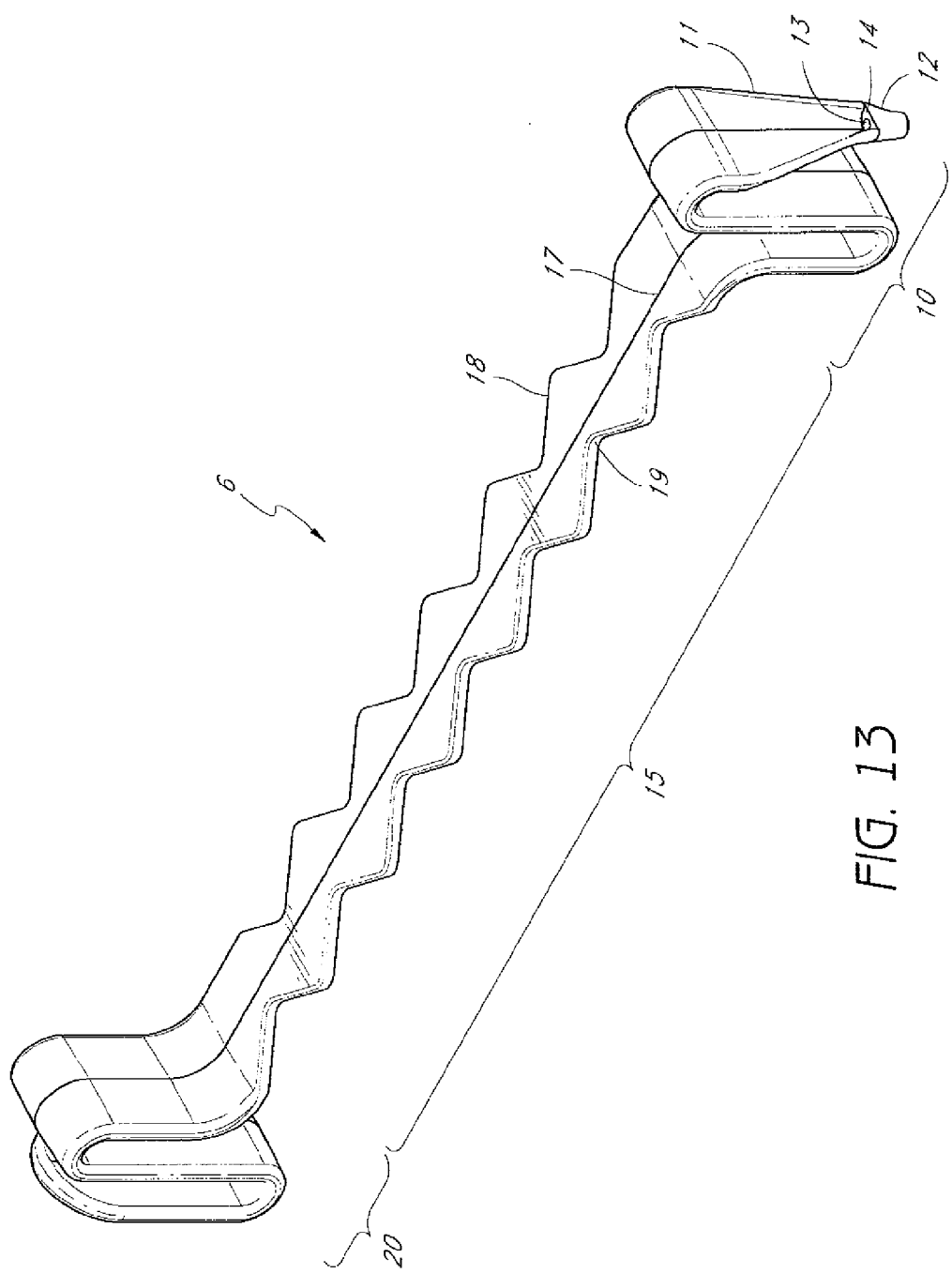
FIG. 13 is a perspective view of a stent that has scalloped edges according to another preferred embodiment of the present invention.
Figure 14:
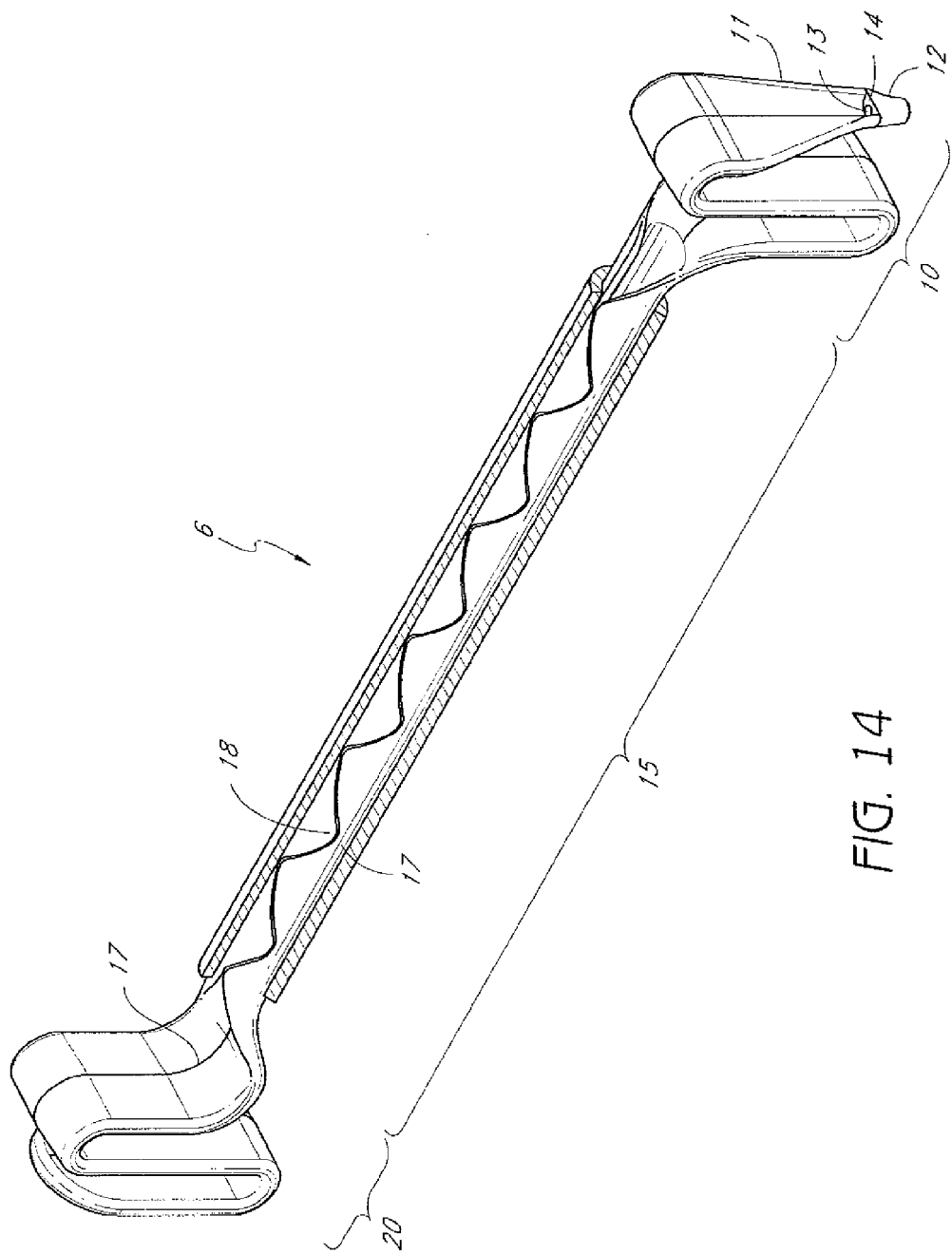
FIG. 14 is a perspective view of the stent from FIG. 13 after the stent has been deployed within a passageway and formed a curled condition.

FIG. 13 is a perspective view of a stent 6 according to another embodiment of the present invention. The stent 6 illustrated in FIG. 13 is similar to the stent illustrated in FIG. 1 except that the edges of the stent 6 in FIG. 13 are scalloped. The edges 18 and 19 of the main body portion 15 include a series of curved projections resulting in a periodic, wavy shape. FIG. 14 is a perspective view of the stent 6 shown in FIG. 13 after the stent 6 has been deployed within a passageway 40. The edges 18 and 19 are formed such that the peaks of the wavy edge 18 fit within the valleys of the wavy edge 19 and vice versa.

Figure 15:
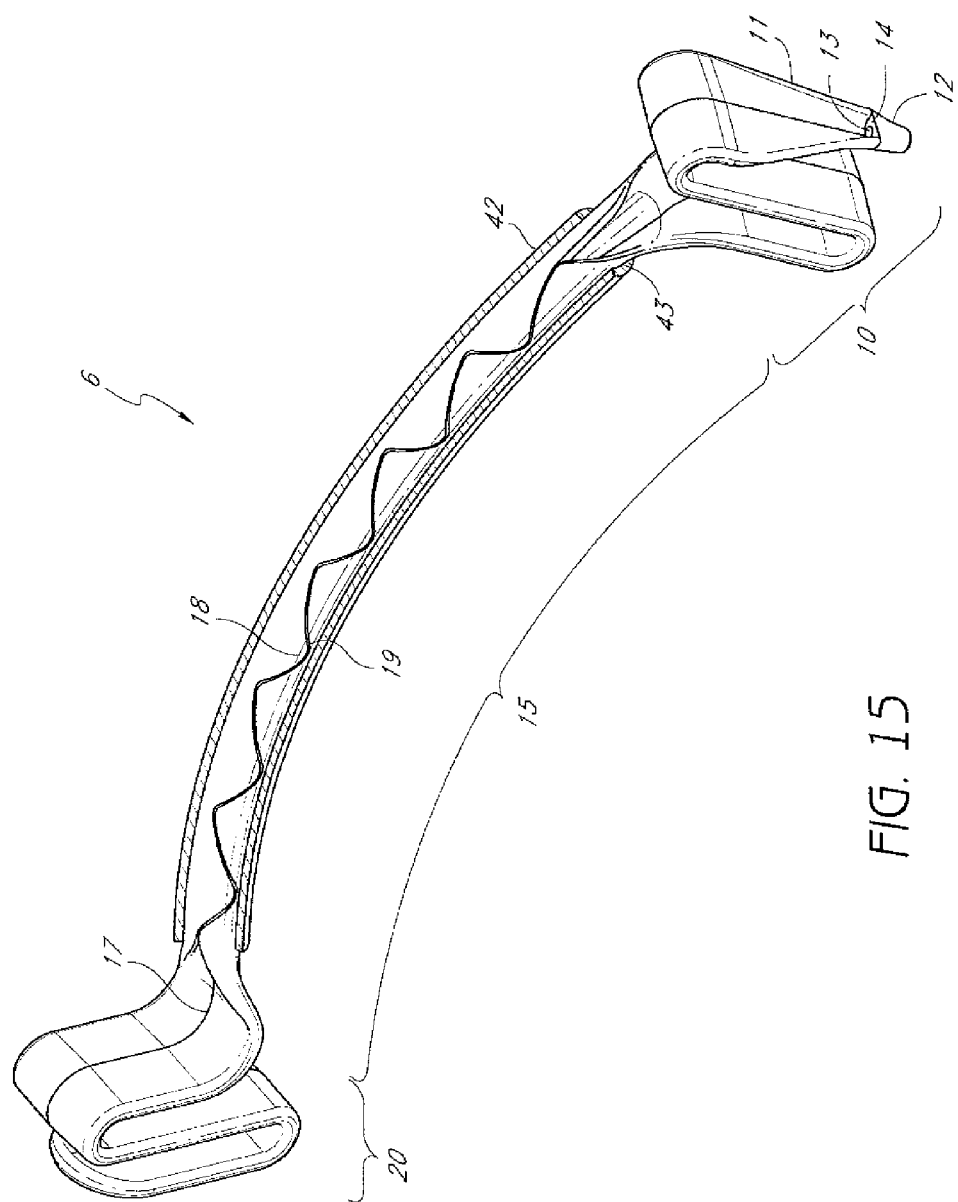
FIG. 15 is a perspective view of the stent from FIG. 14 after the stent has been deployed within a curved passageway.

FIG. 15 is a perspective view of the stent 6 shown in FIG. 14 after the stent 6 has been deployed within a curved passageway 42. The edges 18 and 19 curl towards a center portion 17 of the main body portion of the stent 15 and conform to the inner surface 43 of the curved passageway 42. The scalloped edges 18 and 19 facilitate the stent 6 to form a curved shape along the longitudinal axis.

Figure 16:
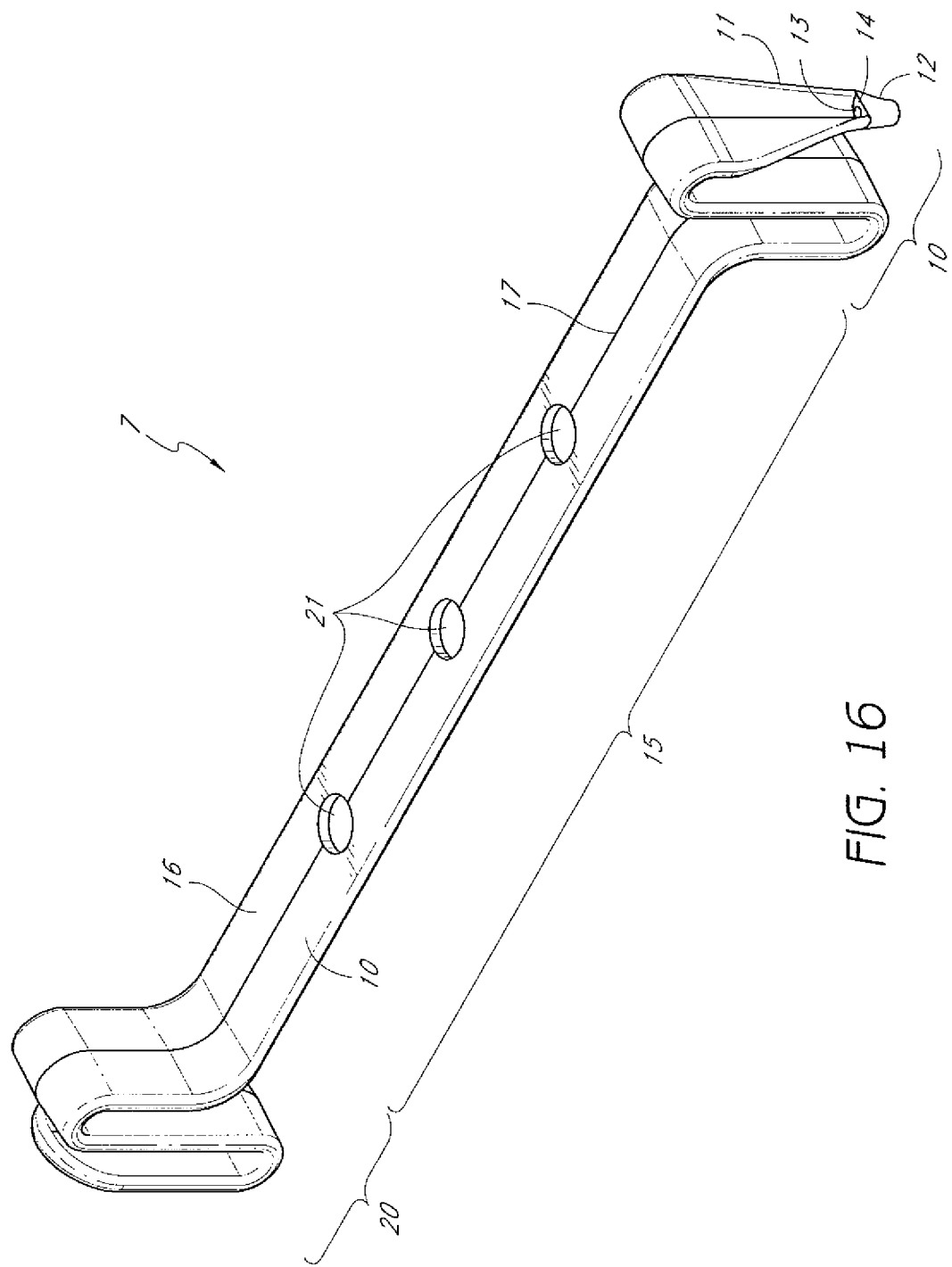
FIG. 16 is a perspective view of a stent according to another preferred embodiment of the present invention and shows openings defined within a center portion of the main body portion of the stent.

FIG. 16 is a perspective view of a stent 7 according to another embodiment and shows openings 21 disposed within a center portion 17 of the main body portion 15. The stent 7 illustrated in FIG. 16 is similar to the stent illustrated in FIG.

Figure 17:
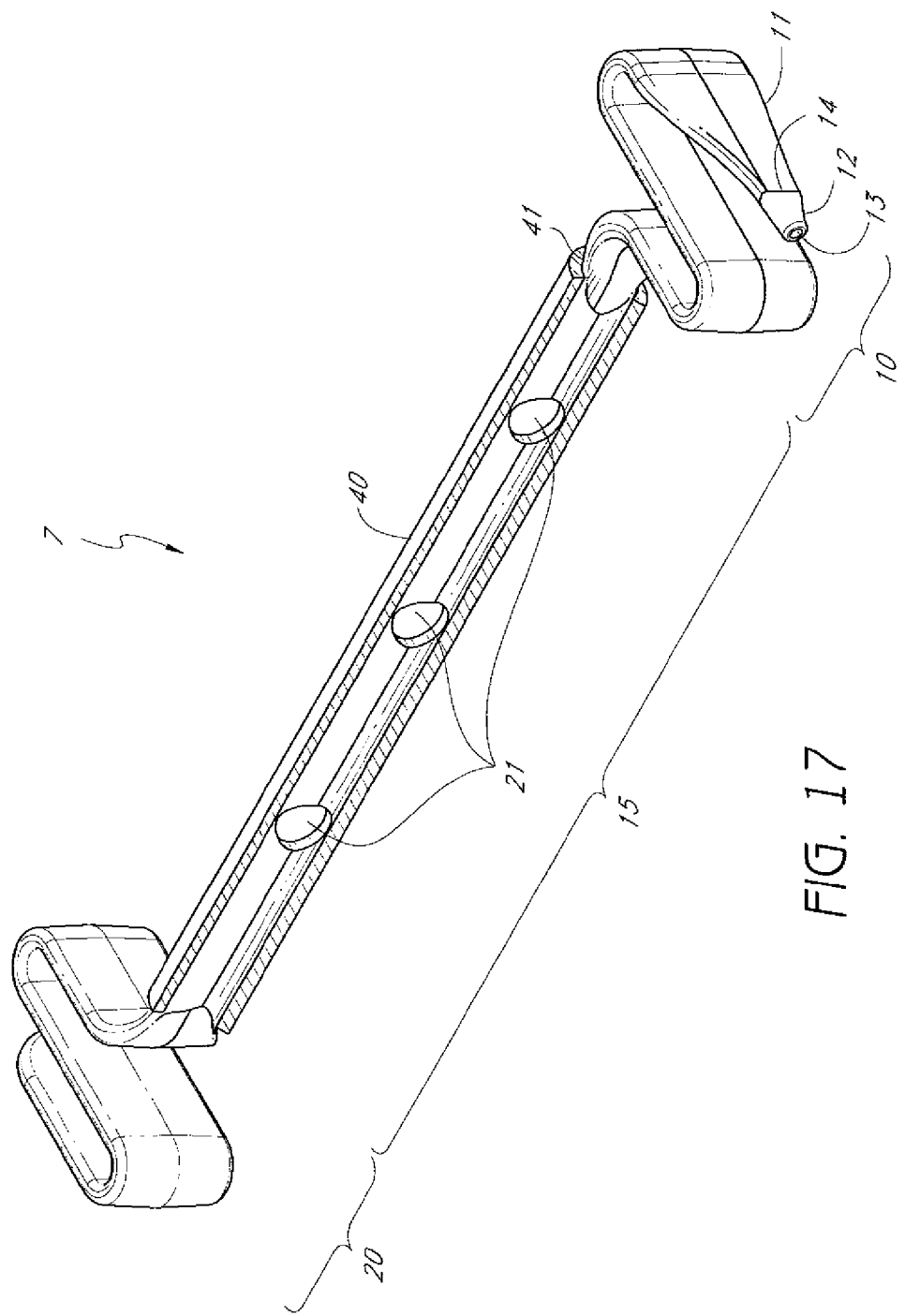
FIG. 17 is a bottom perspective view of the stent illustrated in FIG. 16 after the stent has been deployed within a passageway.

1 except that the body portion 15 includes one or more openings 21. FIG. 17 is a perspective view from the bottom of the stent 7 after the stent has been deployed within a passageway 40. The edge portions 16 of the stent 15 have curled towards the center portion 17 such that the lower surface of the stent 7 conforms to the inner surface 41 of the passageway 40. The openings 21 defined in the center portion 17 may facilitate the drainage of fluids flowing through the body passageway while the stent is deployed.

Figure 18:
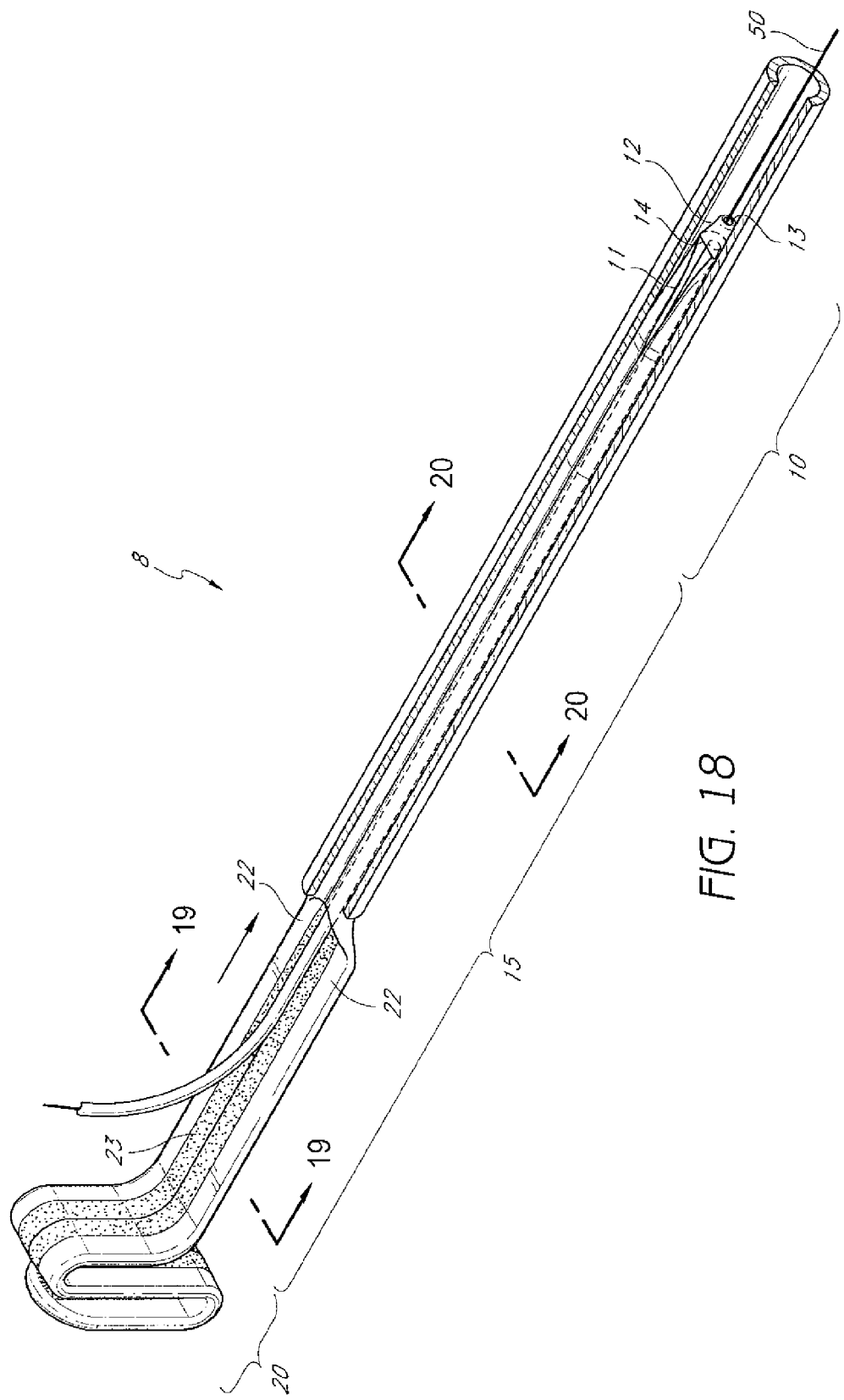
FIG. 18 is a perspective view of another preferred embodiment of the stent and shows the proximal portion curling to conform to an inner surface of the passageway as the stent enters the passageway.

FIG. 18 is a perspective view of a stent 8 according to another embodiment of the present invention. The stent 8 illustrated in FIG. 18 is similar to the stent illustrated in FIG. 1 except that the stent 8 includes at least two different materials. For example, the stent 8 may include a first material for one or more spines 23 that extend along at least a portion of the longitudinal length of the stent 8. The stent 8 may further include a second material that is more flexible than the first material and is used for edge portions 22 on one or both sides of the spine 23. In the illustrated point of insertion, the proximal portion 10 and portions of the main body portion 15 have been pushed into the passageway 40. Passageway 40 has been cutaway to show the deployment of the stent 8 within the passageway 40.

As seen in the cutaway portion of passageway 40, the edge portions 22 of the main body portion 15 of stent 8 curl towards a spine 23 of the stent 8. The lower surface of the main body portion 15 of the stent 8 conforms to the inner surface 41 of the passageway 40. In this embodiment, the edge portions 22 comprise a softer material than the spine 23 to facilitate the edges forming a curved shape while still maintaining a relatively rigid spine 23 along the length of the stent 8. The softer material used in edge portions 22 allowed the edge portions 22 to curl towards the center portion 23 more easily. The more rigid material used for the spine 23 helps the stent 8 to maintain a groove-like or tubular shape when the stent 8 is deployed within the passageway 40. Although only two types of materials are shown, those of skill in the art will understand that more then two types of materials may be used in the stent 8. For example, the edge portions 22 could themselves comprise multiple types of materials, with softer materials being used closer to the edge of the edge portions 22 and more rigid materials being used towards the spine 23. In another example, the spine 23 may comprise a softer material than the edge portions 22.

Figure 20:
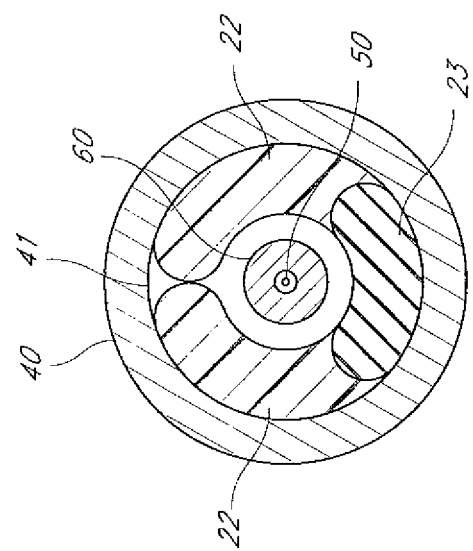
FIG. 20 is a cross-sectional view of a portion of the stent from FIG. 18 taken along the line 20-20 of FIG. 18 after entering the passageway.
Figure 19:
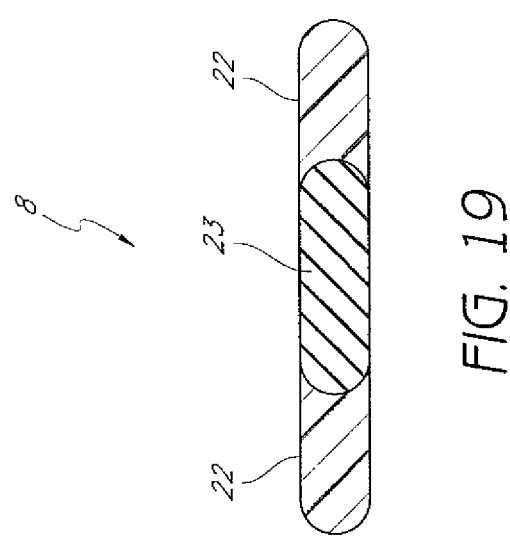
FIG. 19 is a cross-sectional view of a portion of the stent taken along the line 19-19 of FIG. 18 before the portion enters the passageway.

FIG. 19 is a cross-sectional view of a portion of the stent 8 taken along the line 19-19 of FIG. 18 before the portion enters the passageway. The different materials used for the edges 22 and spine 23 are illustrated with different cross-hatching. FIG. 20 is a cross-sectional view of a portion of the stent from FIG. 18 taken along the line 20-20 of FIG. 18 after entering the passageway. As most clearly illustrated in FIG. 20, the edge portions 22 have curled toward the spine 23 of the stent 8 such that the lower surface of the stent 8 conforms to the inner surface 41 of the passageway 40. The softer material of the edge portions 22 facilitates the edge portions 22 to curl towards the spine 23 while the more rigid spine 23 helps maintain the stent 8 in a tubular shape while the stent 8 is deployed within the passageway 40.

FIG. 21 is a side view of a stent 24 according to another preferred embodiment of the present invention and shows thicknesses, T1 and T2, of the stent varying along the longitudinal length of the stent. For example, the main body portion 15 has a thickness of T1 which is thicker then the thickness T2 of the proximal portion 10 and a distal portion 20. FIG. 22 is a side view of another stent 25 that has a varying thickness along the longitudinal length of the stent. The stent 25 illustrated in FIG. 22 comprises a main body portion 15 that is thinner then a proximal portion 10 and a distal portion 20 of the stent 25. The main body portion 15 has a thickness of T3 which is thinner then the thickness T4 of the proximal portion 10 and a distal portion 20. The varying thickness of the proximal portion 10, the main body portion 15 and the distal portion 20 facilitates the stent to maintain its structure and may further facilitate preventing the stent from migrating. For example, a thicker main body portion 15 may help the stent maintain a tubular structure when the stent is deployed within a passageway. Correspondingly, a thicker proximal portion 19 and a thicker distal portion 20 may help prevent the stent from migrating after it has been deployed. Although not shown in the figures, it will be understood by those of skill in the art that more then portions of the stent may have more then two thicknesses. For example, the proximal portion 10 could have a first thickness, the main body portion 15 could have a second thickness, and the distal portion could have a third thickness.

Figure 23:
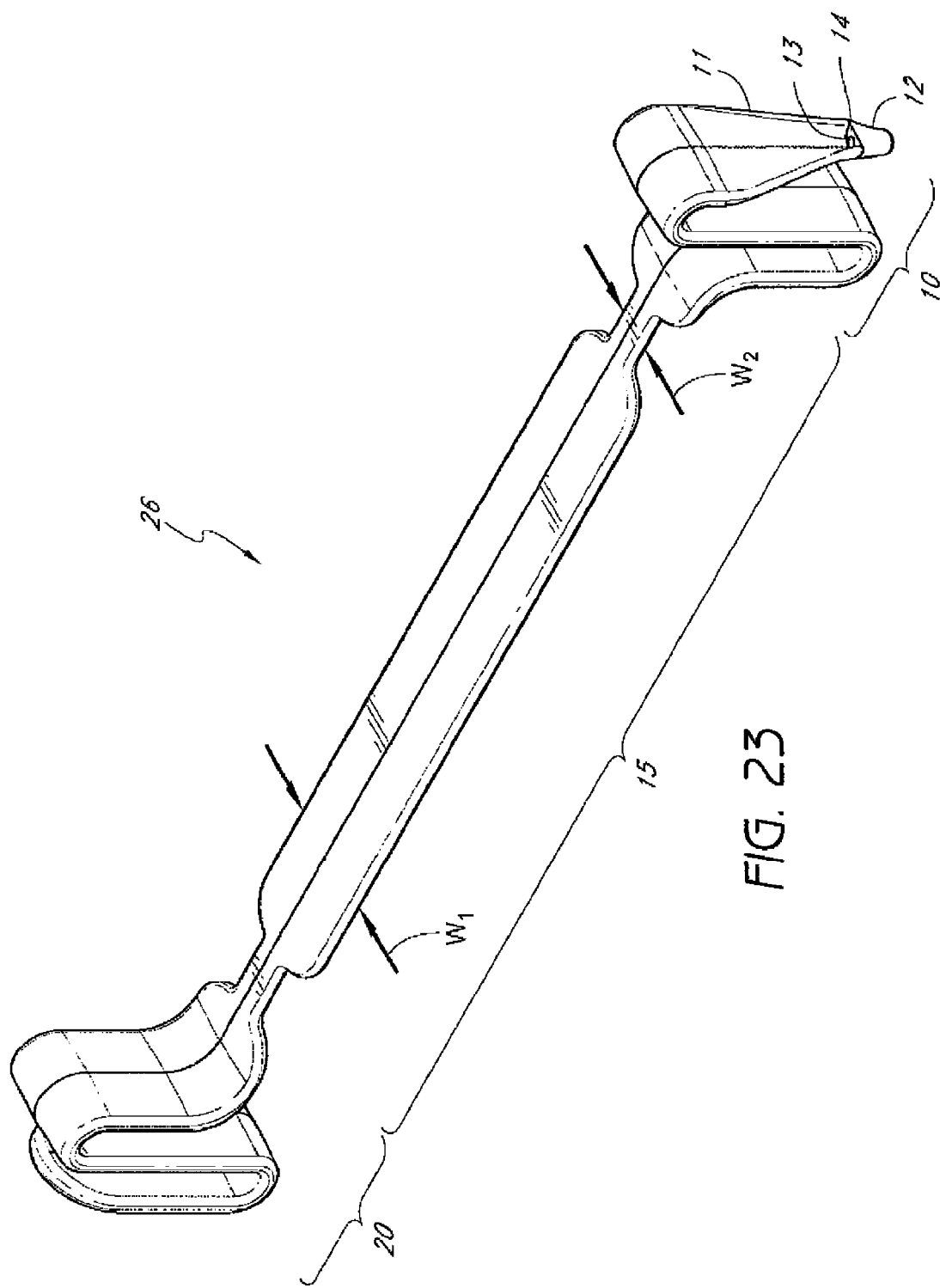
FIG. 23 is a perspective view of a stent according to another preferred embodiment of the present invention and shows widths, W1 and W2, of the stent varying along the longitudinal length of the stent.

FIG. 23 is a perspective view of a stent 26 according to another preferred embodiment of the present invention and shows widths, W1 and W2, of the stent varying along the longitudinal length of the stent. The stent 26 includes a proximal portion 10, a main body portion 15, and a distal portion 20. The main body portion 15 has two different widths. Towards the proximal portion 10 and the distal portion 20, the main body portion 15 has a width W2. The rest of the main body portion 15 has a width of W1. The different widths of the stent 26 help retain the stent in a fixed position and help prevent the stent from migrating when it is deployed within a body passageway. Although not shown various portions of the stent 26 may have varying widths. For example, the main body portion 15 of the stent 25 may have a first width towards the proximal portion 10, a second width between the proximal portion 10 and distal portion 20 and third width towards the distal portion 20.

Figure 24:
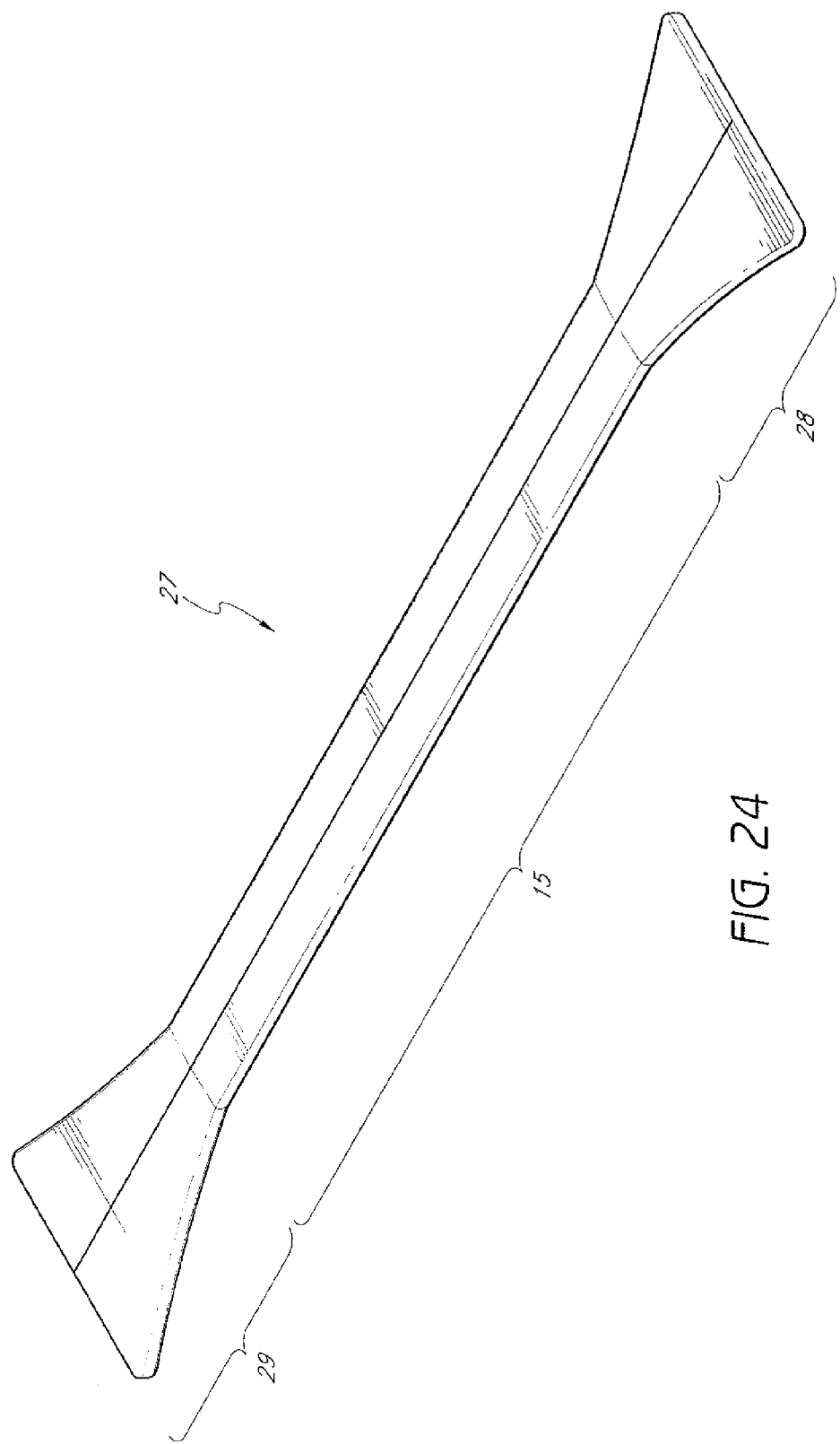
FIG. 24 is a perspective view of a stent according to another preferred embodiment of the present invention showing a tapered proximal portion and a tapered distal portion.

FIG. 24 is a perspective view of a stent 27 according to another preferred embodiment of the present invention showing a tapered proximal portion 28 and a tapered distal portion 29. The proximal portion 28 and distal portion 29 are tapered so as to be wider towards the ends of the stent 27 and thinner towards the center of the stent 27.

Figure 25:
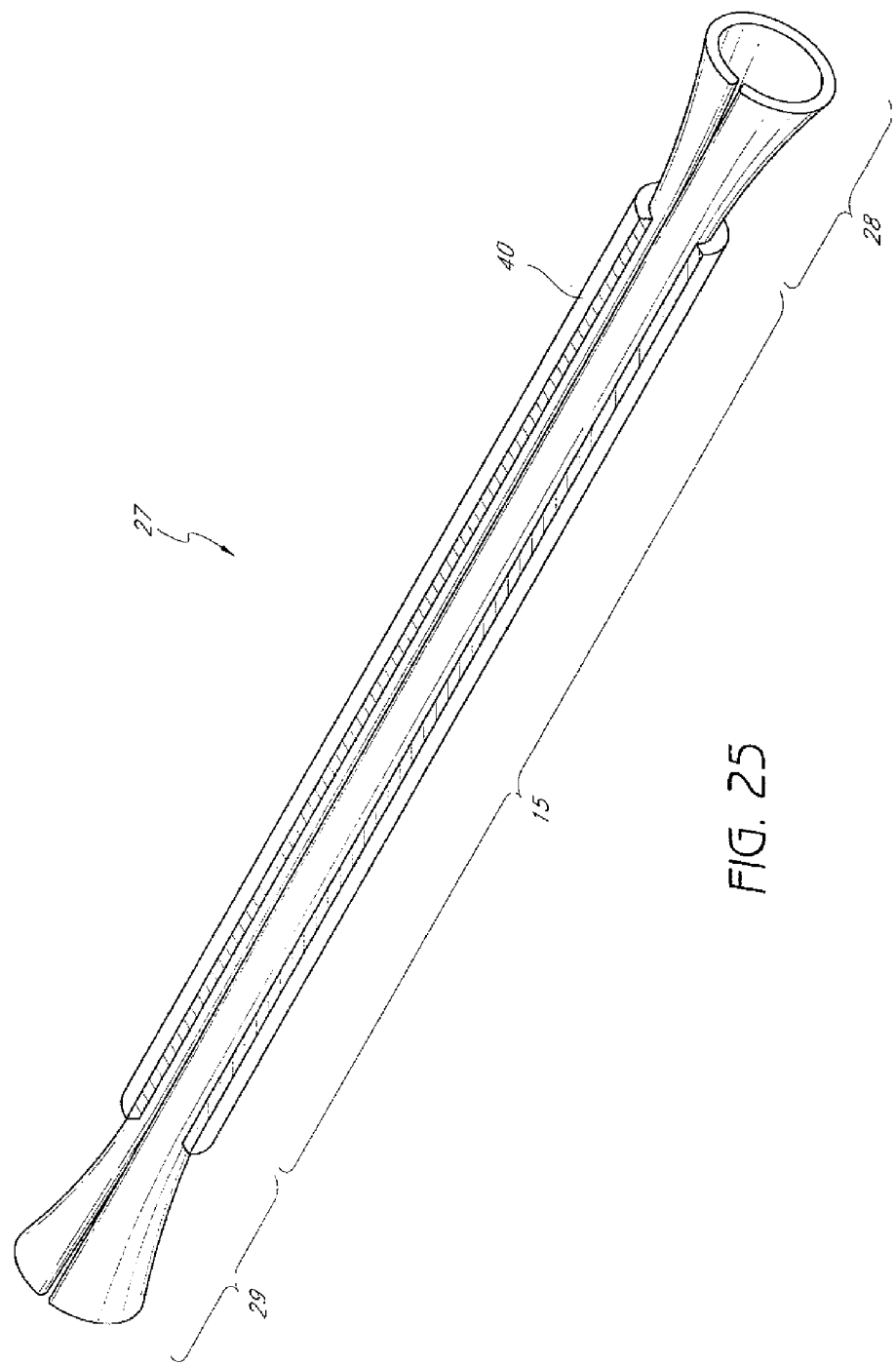
FIG. 25 is a perspective view of the stent from FIG. 24 after the stent has been deployed in a passageway to form a conical shape on both the proximal and distal ends of the stent.

FIG. 25 is a perspective view of the stent 27 from FIG. 24 after the stent has been deployed in a passageway to form a conical shape on both the proximal and distal ends of the stent. The edge portions of the main body portion 15 have curled towards the center portion to form a generally tubular structure. The edges of the tapered proximal portion 28 and the tapered distal portion 29 have also curled towards the center portion to form a cone or conical shaped structure. This cone shaped structure formed by the proximal portion 28 and the distal portion 29 helps prevent migration of the stent when it is deployed. The cone shaped structure also creates a wider opening at the ends of the stent which help when inserting fluids, medical devices and other apparatus into the body passageway 40. The conically shaped ends of the stent 27 may further help the narrower portion of the stent between the ends to maintain a curled shape.

Figure 26:
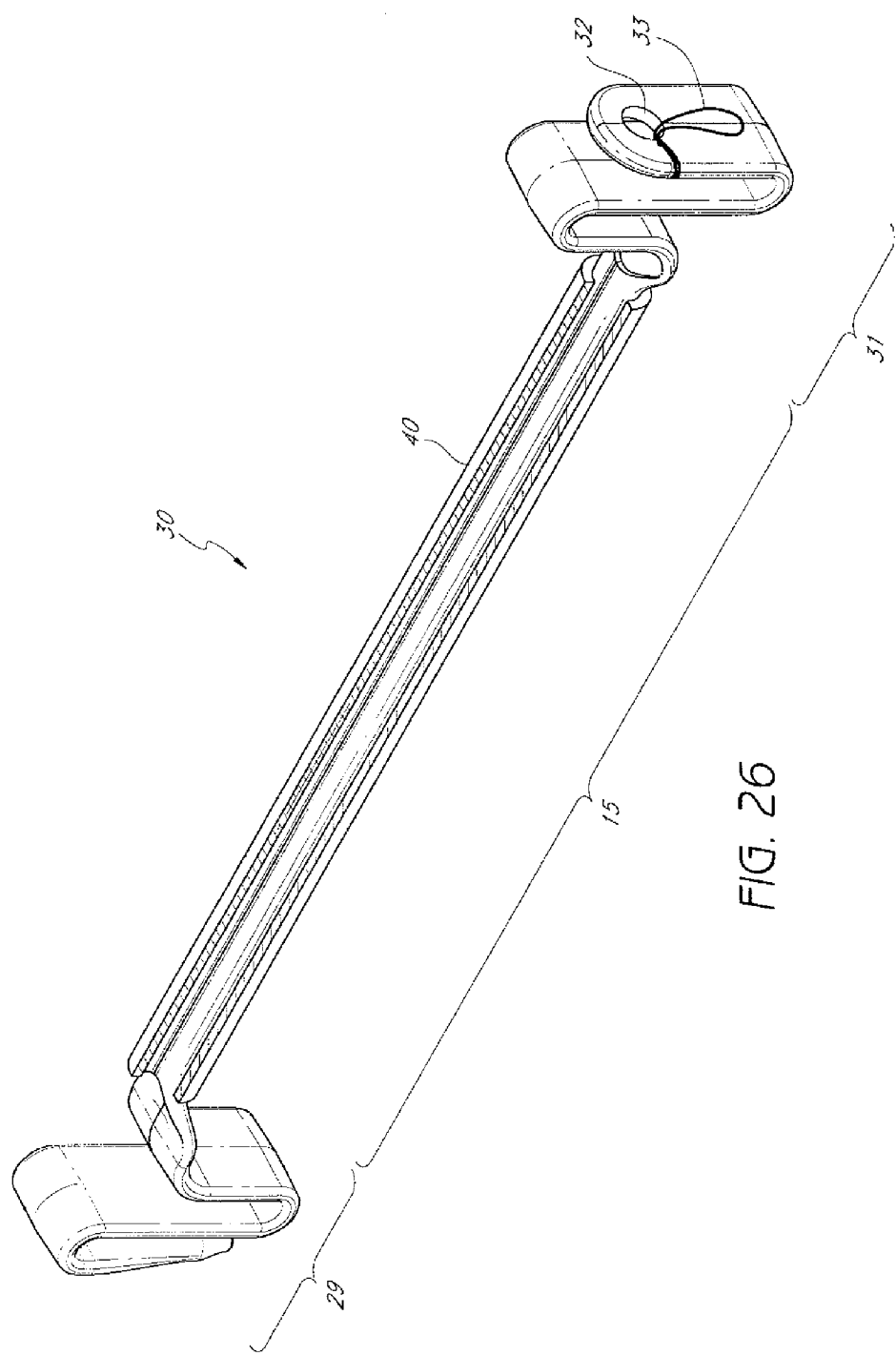
FIG. 26 is a perspective view of a stent according to another preferred embodiment of the present invention and shows a tab or hole configured for receiving a suture or other structure to facilitate removal of the stent from the passageway.

FIG. 26 is a perspective view of a stent according to another preferred embodiment of the present invention and shows a tab, hole, or opening 32 configured for receiving a suture or other structure to facilitate removal of the stent from the passageway. The opening 32 is disposed with the distal portion 31. A suture 33 may be attached to the distal portion 31 by tying the suture 33 though the opening 32. After a stent is no longer needed, the stent may be pulled out of the body passageway using the suture 32. Other devices, such as hooks, may be used to remove the stent.

Figure 27:
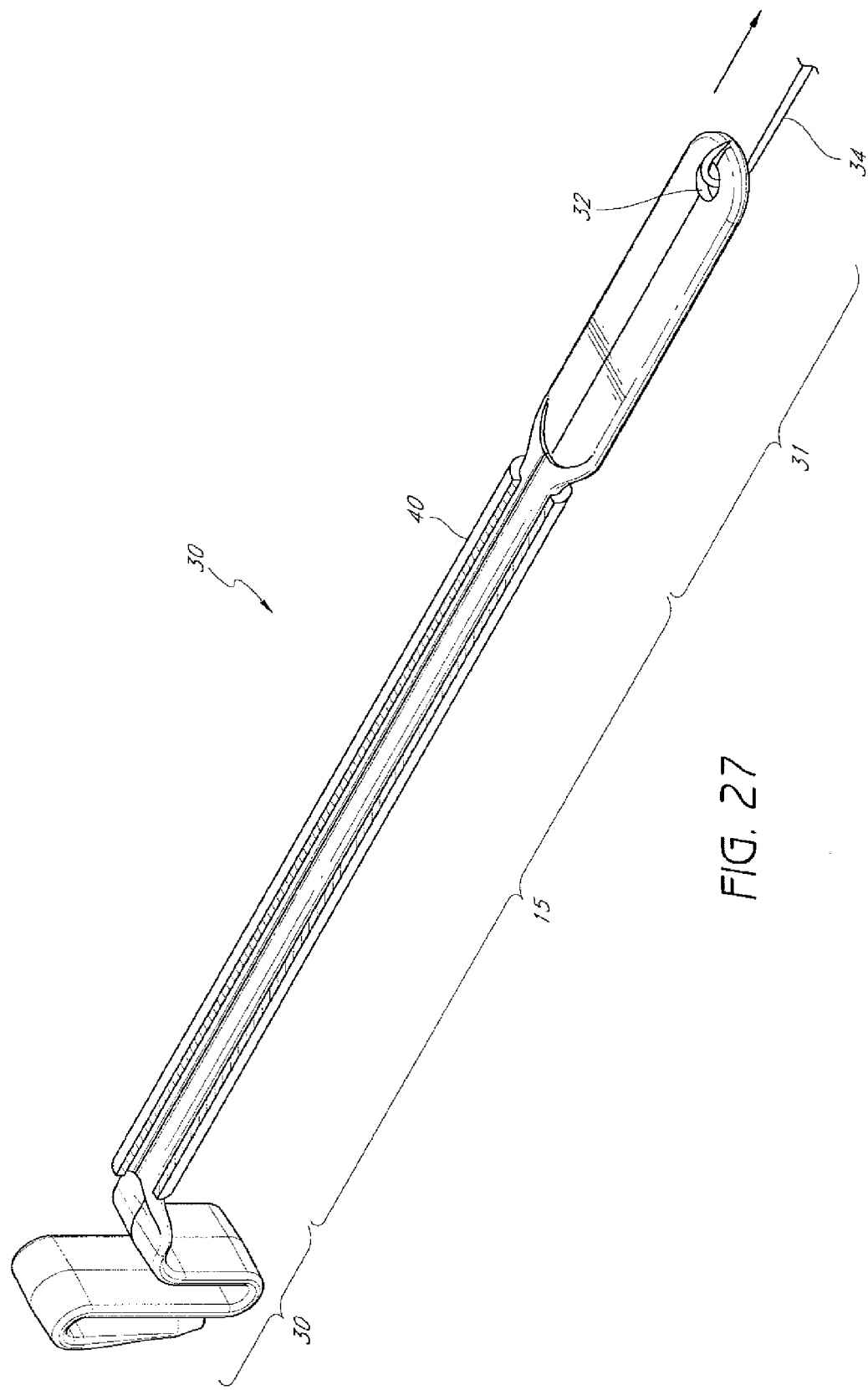
FIG. 27 is a view similar to FIG. 26 except that a hook, not a suture, is in the process of removing the stent from the passageway.

FIG. 27 is a view similar to FIG. 26 except that a hook 34, not a suture, is in the process of removing the stent from the passageway. The retention curve of the distal portion 31 may be pulled straight as the stent is pulled out of a body passageway.

The various embodiments of the stent described above in accordance with the present invention thus provide a means to help strengthen and maintain body passages of the patient before and after operations or medical procedures. The stent may be easily constructed and the same stent may be used for a variety of different diameter body passageways. The stent may also be easily deployed and removed from various body passageways.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. A stent for insertion into a lumen of a patient, comprising:
   a proximal portion;
   a distal portion; and
   a body portion disposed between the proximal and distal portions and having an upper surface and a lower surface, the entire body portion being substantially planar when the body portion is in a delivery state and having lateral edge portions and a center portion, the lateral edge portions being adapted to curl towards the center portion so that a width of the body portion decreases as the body portion is inserted into the lumen.

2. The stent of claim 1, wherein the body portion comprises at least one of silicone, polyurethane, a polyethylene blend, stainless steel, a metal, a metal alloy, and Nitinol materials.

3. The stent of claim 1, wherein the body portion has a curvature when viewed in a cross-section perpendicular to a length of the body portion in the delivery state.

4. The stent of claim 1, wherein at least one of the proximal portion and the distal portion comprises a retention curve.

5. The stent of claim 1 further comprising a guide portion configured to facilitate deployment of the stent within the lumen.

6. The stent of claim 5, wherein the guide portions is configured to receive a push catheter.

7. The stent of claim 1, wherein the proximal portion is tapered to facilitate deployment of the stent within the lumen.

8. The stent of claim 1, wherein at least one of the lateral edge portions comprises a curve.

9. The stent of claim 1, wherein the body portion comprises at least one aperture.

10. The stent of claim 1, wherein the body portion comprises at least two materials, the first material being more rigid than the second material.

11. The stent of claim 1, wherein the body portion has a first thickness, the proximal portion has a second thickness, and the distal portion has a third thickness, and wherein the first thickness is different from at least one of the second and the third thickness.

12. The stent of claim 1, wherein a first portion of the body portion comprises a first width, wherein a second portion of the body portion comprises a second width, and wherein the first width is different from the second width.

13. The stent of claim 1, wherein the distal portion comprises at least one aperture.

14. The stent of claim 1 further comprising a medication layer positioned over at least one of the upper surface and the lower surface so as to dissolve within the lumen.

15. The stent of claim 1, wherein the body portion forms a C-shaped cross-section when in a deployed state.

16. The stent of claim 1, wherein the body portion forms a tubular shape when in a deployed state.

17. The stent of claim 1, wherein the body portion forms a spiral shape such that at least one of the lateral edge portions overlaps the other lateral edge portion when in a deployed state.

18. A self-deploying stent for placement in a lumen of a patient, the stent comprising:
   a body member comprising a pliant material and being movable between a first cross-sectional shape when in a delivery state and a second cross-sectional shape when in a deployed state, the first cross-sectional shape being adapted to have an overall width greater than the second cross-sectional shape and greater than an inside diameter of the lumen, and the body member having lateral edge portions and a center portion, the lateral edge portions being adapted to curl towards the center portion when the body member is moved from the first cross-sectional shape to the second cross-sectional shape while the stent is being inserted into the lumen, the entire body member being substantially planar when the body member is in the first cross-sectional shape.

19. The stent of claim 18, wherein the stent is in the delivery state when the stent is outside the lumen.

20. The stent of claim 18, wherein the stent is in the deployed state when the stent is inside the lumen.

21. A self-deploying stent for placement in a lumen of a patient, the stent comprising:
   a body member being adapted to be movable between a first cross-sectional shape and a second cross-sectional shape so that when a first portion of the body member is disposed inside the lumen and a second portion of the body member is disposed outside the lumen the first portion has the second cross-sectional shape and the second portion has the first cross-sectional shape, the first cross-sectional shape being adapted to have an overall width greater than an inside diameter of the lumen, and wherein the first portion comprises lateral edge portions and a center portion, the lateral edge portions being adapted to curl towards the center portion when the first portion is dispose inside the lumen so that a width of the first portion decreases as the first portion is inserted into the lumen, the entire body member being substantially planar when the body member is in the first cross-sectional shape.

22. The stent of claim 21, wherein the body member comprises a transition region disposed between the first portion and the second portion at least when the stent is being inserted into the lumen, the transition region moving along a length of the stent as the stent is inserted into the lumen but being generally aligned with the opening.

23. A method of using a stent, the method comprising:
aligning a stent having an overall width that is greater than a width of a lumen of a patient with an opening into the lumen;
pushing a portion of the stent through the opening and into the lumen, the portion having lateral edge portions and a center portion, the entire portion being substantially planar before the stent enters the opening; and
as the stent is entering the opening, curling the lateral edge portions towards the center portion of the stent so that a width of the portion decreases before the entire stent is inserted into the lumen.

24. The method of claim 23 further comprising removing the stent from the lumen, wherein the curled lateral edge portions of the stent reverts to a width greater than the width of the lumen when removed from the lumen.

25. A stent for insertion into a lumen of a patient, comprising:
a proximal portion;
a distal portion; and
a body portion disposed between the proximal and distal portions and having an upper surface and a lower surface, the body portion having lateral edge portions and a center portion, the lateral edge portions being adapted to curl towards the center portion so that a width of the body portion decreases as the body portion is inserted into the lumen, wherein the body portion has a first thickness, the proximal portion has a second thickness, and the distal portion has a third thickness, and wherein the first thickness is different from at least one of the second and the third thickness.

26. A stent for insertion into a lumen of a patient, comprising:
a proximal portion;
a distal portion; and
a body portion disposed between the proximal and distal portions and having an upper surface and a lower surface, the body portion having lateral edge portions and a center portion, the lateral edge portions being adapted to curl towards the center portion so that a width of the body portion decreases as the body portion is inserted into the lumen, wherein a first portion of the body portion comprises a first width, wherein a second portion of the body portion comprises a second width, and wherein the first width is different from the second width.

27. A stent for insertion into a lumen of a patient, comprising:
a proximal portion;
a distal portion; and
a body portion disposed between the proximal and distal portions and having an upper surface and a lower surface, the body portion having lateral edge portions and a center portion, the lateral edge portions being adapted to curl towards the center portion so that a width of the body portion decreases as the body portion is inserted into the lumen, wherein the body portion forms a spiral shape such that at least one of the lateral edge portions overlaps the other lateral edge portion when in a deployed state.

* * * * *